US007728137B2

(12) United States Patent
Stössel et al.

(10) Patent No.: US 7,728,137 B2
(45) Date of Patent: Jun. 1, 2010

(54) METAL COMPLEXES

(75) Inventors: Philipp Stössel, Frankfurt (DE); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 118 days.

(21) Appl. No.: 10/548,855

(22) PCT Filed: Mar. 9, 2004

(86) PCT No.: PCT/EP2004/002393

§ 371 (c)(1),
(2), (4) Date: Sep. 9, 2005

(87) PCT Pub. No.: WO2004/081017

PCT Pub. Date: Sep. 23, 2004

(65) Prior Publication Data

US 2006/0220004 A1  Oct. 5, 2006

(30) Foreign Application Priority Data

Mar. 11, 2003  (DE) .................................. 103 10 887

(51) Int. Cl.
*C07F 9/80* (2006.01)
*C07D 333/52* (2006.01)
(52) U.S. Cl. .............................................. 546/3; 549/3
(58) Field of Classification Search ..................... 546/3; 549/3
See application file for complete search history.

(56) References Cited

U.S. PATENT DOCUMENTS

| 4,539,507 | A | 9/1985 | VanSlyke et al. |
| 5,151,629 | A | 9/1992 | VanSlyke |
| 5,679,760 | A | 10/1997 | Mullen et al. |
| 5,763,636 | A | 6/1998 | Kreuder et al. |
| 6,653,438 | B1 | 11/2003 | Spreitzer et al. |
| 7,332,232 | B2 | 2/2008 | Ma et al. |
| 2004/0133004 | A1 | 7/2004 | Stossel et al. |

FOREIGN PATENT DOCUMENTS

| DE | 101 16 962 | 10/2002 |
| DE | 103 04 819 | 8/2004 |
| DE | 103 28 627 | 2/2005 |
| DE | 103 30 761 | 2/2005 |
| EP | 0 070 720 | 1/1983 |
| EP | 0 842 208 | 5/1998 |
| EP | 0 894 107 | 2/1999 |
| EP | 1 028 136 | 8/2000 |
| JP | 9-176629 | 7/1997 |
| WO | WO-92/18552 | 10/1992 |
| WO | WO-98/22148 | 5/1998 |
| WO | WO-00/22026 | 4/2000 |
| WO | WO-00/70655 | 11/2000 |
| WO | WO 0070655 A2 * | 11/2000 |

OTHER PUBLICATIONS

Rheingold et al., "Hydrotris(3-mesitylpyrazol-1-yl)borate and Hydrobis(3-mesitylpyrazol-1-yl)(5-mesitylpyrazol-1-yl)borate: Symmetric and Asymmetric Ligands with Rotationally Restricted Aryl Substituents", *Inorg. Chem.*, vol. 32, pp. 3471-3477 (1993).
López et al., "An H and C NMR spectroscopic study of the structure of potassium and thallium salts of tris- and tetrakis-(pyrazol-1-yl) borates in solution. Some C- B and C- Tl residual coupling constants", *Journal of Organometallic Chemistry*, vol. 503, pp. 265-276 (1995).
Bodar-Houillon et al., "Synthesis and Luminescence Properties of a New Tripode Containing 2,2'-Bipyrazine Subunits: The *tris*-[(6-methyl-2,2'-bipyrazine-2-yl)methyl]amine", *Tetrahedron Letters*, vol. 36, No. 6, pp. 865-868 (1995).
Han et al., "The Tris[3-9-Anthryl)Pyrazol-1-YL]Hydroborato Ligand, [Tp$^{Ant}$]: Compositional Disorder Between a Vacancy and a Chain of Three Atoms", *Polyhedron*, vol. 14, No. 3, pp. 387-391 (1995).
Caris et al., "Synthesis and NMR Study of Two Lipophilic Iron(III) Sequestering Agents Based on 8-Hydroxyquinoline; H-bonding and Conformational Changes", *Tetrahedtron*, vol. 52, No. 13, pp. 4659-4672 (1996).
Armaroli et al., "Luminescence properties of $Eu^{3+}$, $Tb^{3+}$, and $Gd^{3+}$ complexes of the hexadentate N-donor podand tris-[3-(2-pyridyl)pyrazol-1yl]dydroborate", *Chemical Physics Letters*, vol. 276, pp. 435-440 (1997).
Armaroli et al., "Structural and Photophysical Properties of Mononuclear and Dinuclear Lanthanide(III) Complexes of Multidentate Podand Ligands Based on Poly(pyrazolyl)borates", *Inorg. Chem.*, vol. 38, pp. 5769-5776 (1999).
Reeves et al., "Lanthanide complexes of a new sterically hindered potentially hexadentate podand ligand based on a tris(pyrazolyl)borate core; crystal structures, solution structures and luminescence properties", *J. Chem. Soc., Dalton Trans.*, pp. 349-355 (1999).
Piguet et al., "Tridentate binding units as structural patterns for the design of nine-coordinate lanthanide building blocks with predetermined properties", *Journal of Alloys and Compounds*, vol. 303-304, pp. 94-103 (2000).
Woodgate et al., "Synthesis of dioxazaborocines from *N,N'*-alkylbridged-bis(bis(2-hydroxybenzyl)aminomethyl)amines", *Journal of Organometallic Chemistry*, vol. 595, pp. 215-223 (2000).
XXth International Conference on Organometallic Chemistry; Corfu, Jul. 7-12, 2002, Oral Presentations; 0109; C. Slugovc and E. Cremona "Facile Triple C-H Activation Reactions with Iridium-TpPh Complexes", XP002284929 abstract; compounds 1, 2, 3A, 3B.

(Continued)

*Primary Examiner*—Joseph R Kosack
(74) *Attorney, Agent, or Firm*—Connolly Bove Lodge & Hutz LLP

(57) ABSTRACT

The present invention relates to new types of metal complexes. Such compounds can be used as active components (=functional materials) in a series of different types of applications which can be classed within the electronics industry in the widest sense.

The inventive compounds are described by the structure 1 and the formulae (1) to (60).

16 Claims, No Drawings

OTHER PUBLICATIONS

Slugovc et al., "Generation of Heteroatom-Substituted Carbene Complexes of Iridium by Double C-H Activation of Ether and Amine Substrates", *Angew. Chem. Int. Ed.*, vol. 39, No. 12, pp. 2158-2160 (2000).

Slugovc et al., "Investigation of the C-H Activation Potential of [Hydrotris(1*H*-pyrazolato-κ$N^1$)borato(1-)]iridium (IrTp$^x$) Fragments Featuring Aromatic Substituents χat the 3-Position ofthe Pyrazole Rings", *Helvetica Chimica Acta*, vol. 84, pp. 2868-2882 (2001).

Ulrich et al., "Phloroglucinol based podands, versatile tripodal ligands", *Tetrahedron Letters*, vol. 43, pp. 8835-8837 (2002).

Bringmann et al., "The directed synthesis of axially chiral ligands, reagents, catalysts, and natural products through the 'lactone methodology'", *Journal of Organometallic Chemistry*, vol. 661, pp. 49-65 (2002).

Gade, "Transition metal complexes with polydentate amido ligands: novel structural building blocks and chemical reagents", *Journal of Organometallic Chemistry*, vol. 661, pp. 85-94 (2002).

Claramunt et al., "A multinuclear NMR study in the solid state and in solution ofthallium(I) tris-(pyrazol-1-yl)borates (thallium scorpionates)", *Journal of Organometallic Chemistry*, vol. 689, pp. 463-470 (2004).

* cited by examiner

METAL COMPLEXES

RELATED APPLICATIONS

This application is a national stage application (under 35 U.S.C. 371) of PCT/EP2004/002393 filed Mar. 9, 2004 which claims benefit to German application 103 10 887.4 filed Mar. 11, 2003.

Organometallic compounds, especially compounds of the $d^8$ metals, will find use in the near future as active components (=functional materials) in a series of different types of applications which can be classed within the electronics industry in the widest sense. The organic electroluminescent devices based on organic components (for a general description of the construction, see U.S. Pat. No. 4,539,507 and U.S. Pat. No. 5,151,629) and their individual components, the organic light-emitting diodes (OLEDs), have already been introduced onto the market, as demonstrated by the available car radios having organic displays from Pioneer. Further products of this type will shortly be introduced. In spite of all of this, distinct improvements are still necessary here for these displays to provide real competition to the currently market-leading liquid crystal displays (LCDs) or to overtake them.

A development in this direction is the improvement of electron transport materials and blue singlet emitters based on metal chelate complexes, of which aluminum and lanthanum chelate complexes in particular are of interest here.

A further development which has emerged in recent years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4-6].

For theoretical reasons relating to spin probability, up to four times the energy efficiency and power efficiency are possible using organometallic compounds as phosphorescence emitters. Whether this new development will establish itself depends strongly upon whether corresponding device compositions can be found which can also utilize these advantages (triplet emission=phosphorescence compared to singlet emission=fluorescence) in OLEDs. The essential conditions for practical use are in particular a long operative lifetime, a high stability against thermal stress and a low use and operating voltage, in order to enable mobile applications.

In both cases, there has to be efficient chemical access to the corresponding chelate complexes or organometallic compounds. However, it is of particular interest against the background of the rarity of the metals in the case of ruthenium, osmium, rhodium, iridium and gold compounds.

The literature has to date described two basic designs of OLEDs which have fluorescence or phosphorescence emitters as coloring components:

Type 1 typically has the following layer structure [using the example of an OLED with phosphorescence emitter: M. E. Thompson et al., Proceedings of SPIE, 31.07- 02.08.2000, San Diego, USA, Volume 4105, page 119-124]:

1. Carrier plate=substrate (typically glass or plastics films).
2. Transparent anode (typically indium tin oxide, ITO).
3. Hole transport layer (HTL): typically based on triarylamine derivatives.
4. Emitter layer (EL): this layer consists either of a fluorescence emitter or phosphorescence emitter or a matrix material which is doped with the fluorescence emitter or phosphorescence emitter.
5. Electron transport layer (ETL): usually based on tris(8-hydroxyquinolinato)aluminum(III) ($AlQ_3$).
6. Cathode: here, generally metals, metal combinations or metal alloys with a low work function are used, for example Al—Li.

Type 2 typically has the following layer structure [using the example of an OLED with phosphorescence emitter: T. Tsutsui et al. Jpn. J. Appl. Phys., 1999, 38, L 1502-L 1504]:

1. Carrier plate=substrate (typically glass or plastics films).
2. Transparent anode (typically indium tin oxide, ITO).
3. Hole transport layer (HTL): typically based on triarylamine derivatives.
4. Matrix and emitter layer (EL): this layer consists of a matrix material, for example based on triarylamine derivatives, which is doped with the fluorescence emitter or phosphorescence emitter.
5. Electron transport/hole-blocking layer (HBL): typically based on nitrogen heterocycles or based on metal complexes, for example bis(2-methyl-8-hydroxyquinolinato)(4-phenylphenolato)-aluminum(III) (B—$AlQ_3$).
6. Electron transport layer (ETL): usually based on tris(8-hydroxyquinolinato)aluminum(III) ($AlQ_3$).
7. Cathode: here, generally metals, metal combinations or metal alloys with a low work function are used, for example Al.

It is also possible to emit the light through a thin transparent cathode. These devices are appropriately (depending on the use) structured, contacted and finally hermetically sealed, since the lifetime of such devices is generally drastically shortened in the presence of water and/or air.

The characteristic data of the above-described OLEDs show weaknesses including the following:

1. The operative lifetime is in most cases still much too short, which is an obstacle to introduction of OLEDs on the market.
2. It is evident from the efficiency-brightness curves that the efficiency frequently decreases greatly with increasing brightness. This means that the high brightnesses needed in practice can be achieved only by means of a high power consumption. However, high power consumptions require high battery power of portable units (mobile phones, laptops, etc.). Moreover, the high power consumption, which is to a large part converted to heat, can lead to thermal damage to the display.

In the above-illustrated OLED device, the abovementioned function materials have been or are being intensively optimized.

For some time, (pseudo)octahedral metal complexes in the widest sense have been used as the ETL (e.g. $AlQ_3$, see: C. W. Tang et al., Applied Phys. Lett. 1987, 51(12), 913), HBL (e.g. B—$AlQ_3$, see: R. Kwong et al., Applied Physics Letters 2002, 81(1), 162), as the matrix material in the EL (e.g. B—$AlQ_3$, see: C. H. Chen et al., Proceedings of SPIE—The International Society for Optical Engineering 1998, 3421 (Display Technologies II), 78), as the singlet emitter (e.g. $AlQ_3$ and other complexes, see: S. Tokito et al., Synthetic Metals 2000, 111-112, 393) and as the triplet emitter (e.g. Ir(PPy)$_3$, see: WO 00/70655; e.g. Ir(TPy)$_3$ and Ir(BTPy)$_3$, see: S. Okada et al., Proceedings of the SID, 2002, 52.2, 1360). In addition to the individual weaknesses specific to each material, the known metal complexes have general weaknesses which will be presented briefly below:

1. Many of the known metal complexes, in particular those which include main group metals such as aluminum, have a sometimes considerable hydrolysis sensitivity which can have such an extent that the metal complex is decomposed noticeably even after short exposure to air. Others, in contrast, for example the $AlQ_3$ used as an electron transport material, tends to add on water.

The high hygroscopicity of these and similar aluminum complexes is a crucial practical disadvantage. $AlQ_3$ which is synthesized and stored under standard conditions still contains, in addition to the hydroxyquinoline ligands, one molecule of water per complex molecule [cf., for example: H. Schmidbaur et al., Z. Naturforsch. 1991, 46b, 901-911]. This is extremely difficult to remove. For use in OLEDs, $AlQ_3$ therefore has to be purified in a costly and inconvenient manner in complicated, multistage sublimation processes, and stored and handled thereafter with exclusion of water in a protective gas atmosphere. Moreover, large variations in the quality of individual $AlQ_3$ batches, and also poor storage stability were found (see: S. Karg, E-MRS. Konferenz 30.5.00-2.6.00 Strasbourg).

2. Many of the known metal complexes have a low thermal stability. In a vacuum deposition of the metal complexes, this inevitably always leads to the release of organic pyrolysis products, some of which considerably reduce the operative lifetime of the OLEDs even in small amounts.

3. Virtually all of the metal complexes which have been detailed in the literature and have to date found use in OLEDs are homoleptic, (pseudo)octahedral complexes consisting of a central metal coordinated to three bidentate ligands. Complexes of this design can occur in two isomeric forms, the meridional and the facial isomer. Frequently, there is only a slight thermodynamic preference for one of the two isomers. Under certain conditions, for example a certain sublimation temperature, this leads to one or the other isomer or even mixtures of the two occurring. This is not desired, since the two isomers often differ distinctly in their physical properties (emission spectrum, electron and hole conduction properties, etc.), and the properties of an OLED can thus deviate distinctly from one another even in the event of small changes in the preparation process. An example thereof are the distinctly different properties of mer-$AlQ_3$ and fac-$AlQ_3$ which exhibit green and blue photoluminescence respectively (see M. Coelle, Chemical Communications, 2002, 23, 2908-2909).

There is therefore a need for alternative compounds which do not have the abovementioned weaknesses but are in no way inferior in efficiency and emission color to the known metal complexes.

It has now been found that, surprisingly, metal complexes of polypodal ligands display outstanding properties when used as the ETL, as the HBL, as the matrix material in the EL, as the singlet emitter and also as the triplet emitter, the particular specific function being determined by the suitable selection of the metal and of the suitable accompanying ligand. These compounds form the subject matter of the present invention. The compounds feature the following general properties:

1. In contrast to many known metal complexes which are subject to partial or complete pyrolytic decomposition in the course of sublimation, the inventive compounds feature high thermal stability. When used in appropriate devices, this stability leads to a distinct increase in the operative lifetime.

2. The inventive compounds do not have any noticeable hydrolysis or hygroscopicity. Storage for several days or weeks with ingress of air and water vapor does not lead to any changes in the substances. It was not possible to detect addition of water to the compounds. This has the advantage that the substances can be purified, transported, stored and prepared for use under simpler conditions.

3. The inventive compounds, used as the ETL material in the electroluminescent devices, lead to high efficiencies which are in particular independent of the current densities used. This enables very good efficiencies even at high current densities.

4. The inventive compounds, used as the HBL material in the electroluminescent devices, lead to high efficiencies which are in particular independent of the current densities used. This enables very good efficiencies even at high current densities, i.e. high brightnesses. Moreover, the inventive materials are stable toward holes, which is not the case to a sufficient degree, for example, for other metal complexes, for example $AlQ_3$ and analogous compounds (see, for example: Z. Popovic et al., Proceedings of SPIE, 1999, 3797, 310-315).

5. The inventive compounds, used in electroluminescent devices as the EL material in pure form or as the matrix material in combination with a dopant, lead therein to high efficiencies, the electroluminescent devices being notable for steep current-voltage curves and particularly for long operative lifetime.

6. The inventive compounds can be prepared with good reproducibility in reliably high yield and do not have any variation between batches.

7. Some of the inventive compounds have excellent solubility in organic solvents. This allows these materials to be purified more readily and also makes them processable from solution by coating or printing techniques. In the customary processing by evaporation too, this property is advantageous, since the purification of the units or of the shadow masks used is thus considerably eased.

The class of chelate complexes and organometallic compounds of polypodal ligands which are described in more detail below and their use as functional materials in electrooptical components is novel and has to date not been described in the literature, but their efficient preparation and availability as pure materials is of great significance for this purpose.

The present invention thus provides metal complexes of the structure 1

structure 1 containing at least one metal Met coordinated to a polypodal ligand Lig of the structure 2,

structure 2 where V is a bridging unit, characterized in that it contains from 1 to 80 atoms and the three part-ligands L1, L2 and L3 which may be the same or different at each instance are covalently bonded to one another, and where the three part-ligands L1, L2 and L3 satisfy the structure 3

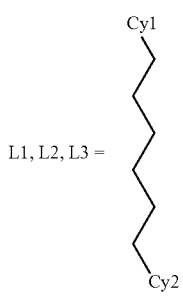

structure 3 where Cy1 and Cy2 are the same or different at each instance and correspond to substituted or unsubstituted, saturated, unsaturated or aromatic homo- or heterocycles or part-homo- or part-heterocycles of a fused system, which are each bonded ionically, covalently or coordinatively to the metal via a ring atom or via an atom bonded exocyclically to the homo- or heterocycle.

The bridging unit V has from 1 to 80 atoms from main group III, IV and/or V of the elements of the periodic table. These form the basic skeleton of the bridging unit.

The zig-zag line symbol selected above describes here the linkage of Cy1 to Cy2 only in general terms. A more detailed description of the possible linkages of the cycles is given below.

The homo- or heterocycles Cy1 and Cy2 may be linked via a single bond. Moreover, the part-homo- or part-heterocycles Cy1 and Cy2 may be linked via a common edge. Furthermore, in addition to the linkage via a single bond or a common edge, they may be linked to one another via substituents on the homo- or heterocycles Cy1 and Cy2 or the part-homo- or part-heterocycles, and thus form a polycyclic, aromatic or aliphatic ring system.

The linkages possible in principle will be shown here by way of example using the example of a benzene ring (Cy1) and of a pyridine (Cy2) (see FIG. 1) without any intention thus to restrict the multitude of all possible linkages.

Scheme A:

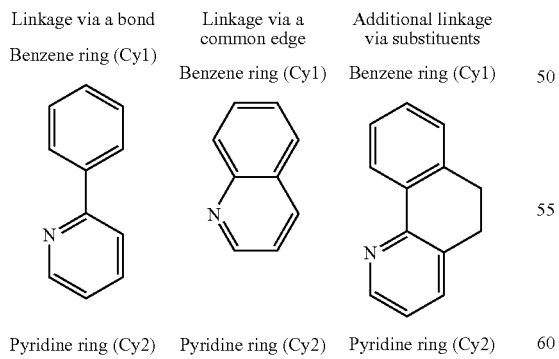

Preference is given to inventive compounds of the structure 1, characterized in that they are uncharged i.e. are externally electrically neutral.

Preference is given to inventive compounds of the structure 1, characterized in that at least one of the part-ligands L1, L2 and L3, preferably at least two of the part-ligands L1, L2 and L3, and more preferably all three part-ligands L1, L2 and L3 are singly negatively charged.

Preference is given to inventive compounds of the structure 1, characterized in that L1=L2=L3.

Preference is likewise given to inventive compounds of the structure 1, characterized in that L2≠L2.

Preference is further given to inventive compounds of the structure 1, characterized in that Cy1 is different from Cy2.

Preference is given to inventive compounds of the structure 1, characterized in that the linking unit V contains, as the linking atom, an element of main group 3, 4 or 5, or a 3- to 6-membered homo- or heterocycle.

Preference is given to inventive compounds of the structure 1, characterized in that the polypodal ligand Lig of the structure 4 generates facial coordination geometry on the metal Met.

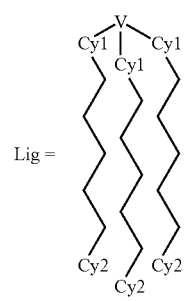

structure 4

Preference is likewise given to inventive compounds of the structure 1, characterized in that the polypodal ligand Lig of the structure 5 generates meridional coordination geometry on the metal Met.

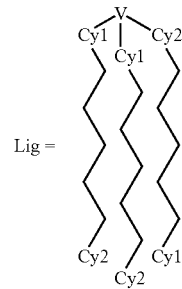

structure 5

In the context of this application, facial and meridional coordination describe the environment of the metal Met with the six donor atoms. Facial coordination is present when three identical donor atoms occupy a triangular surface in the (pseudo)octahedral coordination polyhedron, and three identical donor atoms other than the first three occupy another triangular surface in the (pseudo)octahedral coordination polyhedron. Analogously, a meridional coordination is understood to be one in which three identical donor atoms occupy one meridian in the (pseudo)octahedral coordination polyhedron, and three identical donor atoms other than the first three occupy the other meridian in the (pseudo)octahedral coordination polyhedron. This will be shown below by way of example with reference to an example of a coordination of three nitrogen donor atoms and three carbon donor atoms (see FIG. 2). Since this description relates to donor atoms and not to the cycles Cy1 and Cy2 which provide these donor atoms, the three cycles Cy1 and the three cycles Cy2 may be the same or different at each instance and nevertheless correspond to a facial or meridional coordination in the context of this application.

Identical donor atoms are understood to be those which consist of the same elements (e.g. nitrogen), irrespective of whether these elements are incorporated within different structures or cyclic structures.

Scheme B:
Facial and meridional coordination using
example of three nitrogen donor atoms and three carbon donor atoms facial coordination    meridional coordination Preference is given in particular to metal complexes according to the compounds (1) to (8) with facial coordination geometry on the metal according to Scheme 1

Scheme 1:

compounds (1)

compounds (2)

compounds (3)

compounds (4)

compounds (5)

compounds (6)

compounds (7)

compounds (8)

where the symbols and indices are each defined as follows:

M is Al, Ga, In, Tt, P, As, Sb, Bi, Sc, Y, La, V, Nb, Ta, Cr, Mo, W, Fe, Ru, Os, Co, Rh, Ir, Cu, Au, Pr, Nd, Sm, Eu, Gd, Tb, Dy, Ho, Er, Tm, Yb, Lu;

L is the same or different at each instance and is C, N, P;

Q is the same or different at each instance and is O, S, Se, Te, N;

T is the same or different at each instance and is N, P, C;

X is the same or different at each instance and is CR, N, P;

Y is the same or different at each instance and is $NR^1$, O, S, Se, Te, SO, SeO, TeO, $SO_2$, $SeO_2$, $TeO_2$;

Z is B, BR, $B(CR_2)_3$, $B(CR_2CR_2)_3$, CR, COH, $COR^1$, CF, CCl, CBr, C—I, $CNR^1_2$ $RC(CR_2)_3$, $RC(CR_2CR_2)_3$, $RC(SiR_2)_3$, $RC(SiR_2CR_2)_3$, $RC(CR_2SiR_2)_3$,

RC(SiR$_2$SiR$_2$)$_3$, cis,cis-1,3,5-cyclohexyl, 1,3,5-(CR$_2$)$_3$ C$_6$H$_3$, SiR, SiOH, SiOR$^1$, RSi(CR$_2$)$_3$, RSi(CR$_2$CR$_2$)$_3$, RSi (SiR$_2$)$_3$, RSi(SiR$_2$CR$_2$)$_3$, RSi(CR$_2$SiR$_2$)$_3$, RSi(SiR$_2$SiR$_2$)$_3$, N, N(CR$_2$)$_3$, N(C=O)$_3$, N(CR$_2$CR$_2$)$_3$, NO, P, As, Sb, Bi, PO, AsO, SbO, BiO, PSe, AsSe, SbSe, BiSe, PTe, AsTe, SbTe, BiTe;

R is the same or different at each instance and is H, F, Cl, Br, I, NO$_2$, CN, a straight-chain or branched or cyclic alkyl or alkoxy group having from 1 to 20 carbon atoms, in which one or more nonadjacent CH$_2$ groups may be replaced by —R$^1$C=CR$^1$—, —C≡C—, Si(R$^1$)$_2$, Ge(R$^1$)$_2$, Sn(R$^1$)$_2$, C=O, C=S, C=Se, C=NR$^1$, —O—, —S—, —NR$^1$— or —CONR$^1$—, and in which one or more hydrogen atoms may be replaced by F, or an aryl or heteroaryl group which has from 1 to 14 carbon atoms and may be substituted by one or more nonaromatic R radicals, where a plurality of substituents R, both on the same ring and on the two different rings, together may in turn form a further mono- or polycyclic, aliphatic or aromatic ring system;

R$^1$ is the same or different at each instance and is an aliphatic or aromatic hydrocarbon radical having from 1 to 20 carbon atoms;

c is the same or different at each instance and is 0 or 1.

Furthermore, preference is likewise given to the compounds (9) to (12) with meridional coordination geometry on the metal according to Scheme 2

Scheme 2:

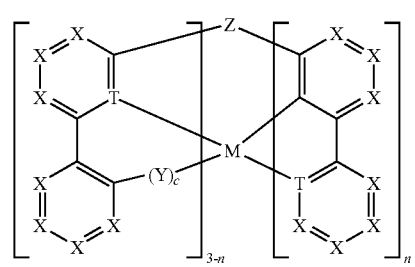

compounds (9)

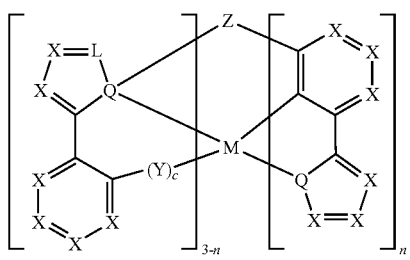

compounds (10)

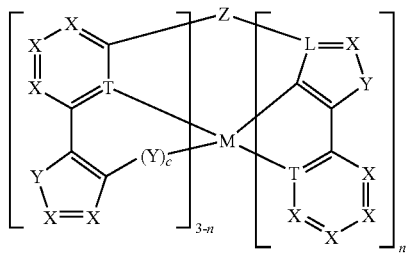

compounds (11)

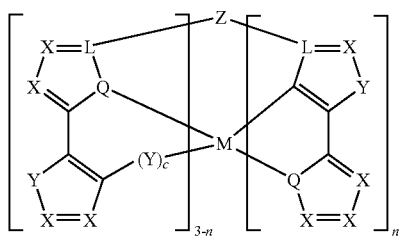

compounds (12)

where the symbols and indices M, L, Q, T, X, Y, Z, R, R$^1$ and c are each as defined in Scheme 1, and where: n is 1 or 2.

The invention further likewise provides compounds which simultaneously have part-ligands of the type as in compounds (1), (2), (3) and/or (4), i.e. mixed ligand systems. These are described by the formulae (13) to (30) according to Scheme 3:

Scheme 3:

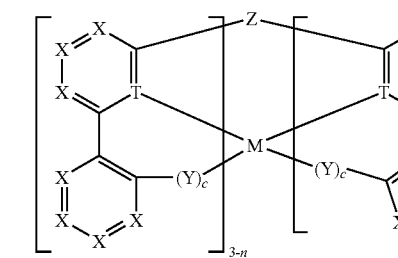

compounds (13)

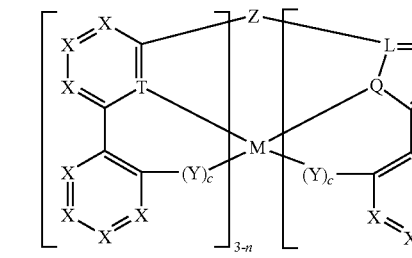

compounds (14)

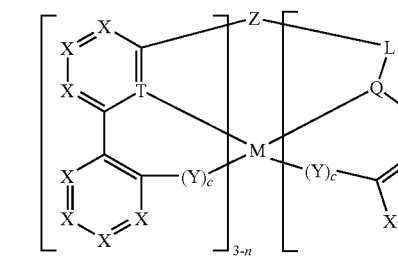

compounds (15)

compounds (16)
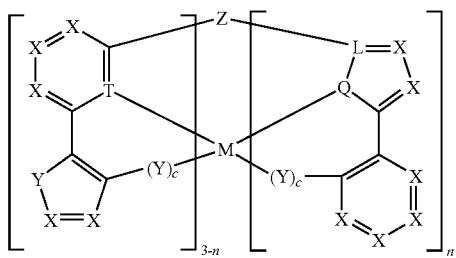
compounds (17)
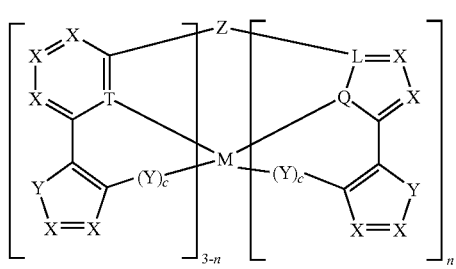
compounds (18)
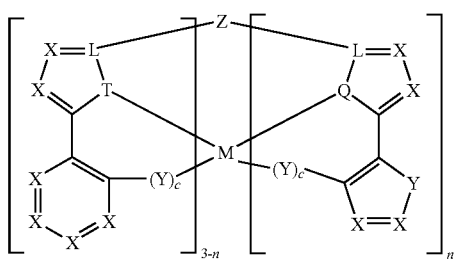
compounds (19)
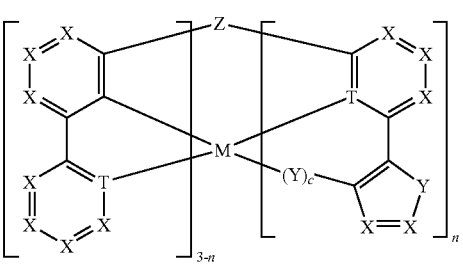
compounds (20)
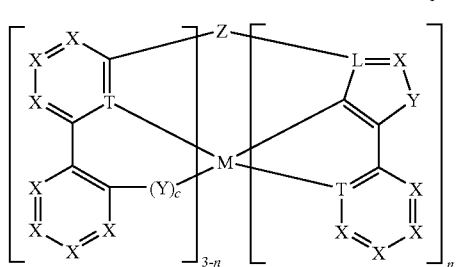
compounds (21)
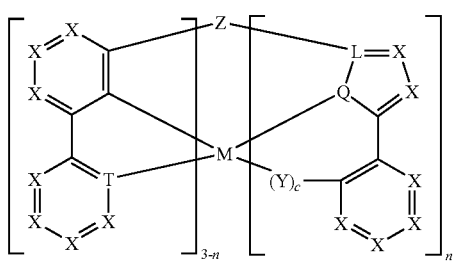
compounds (22)
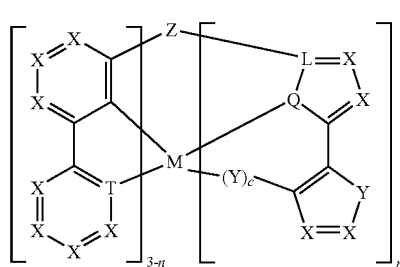
compounds (23)
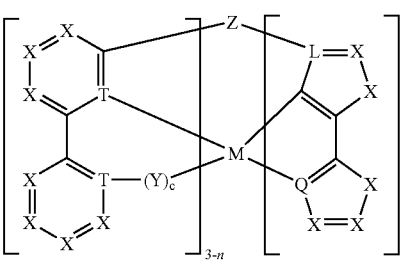
compounds (24)
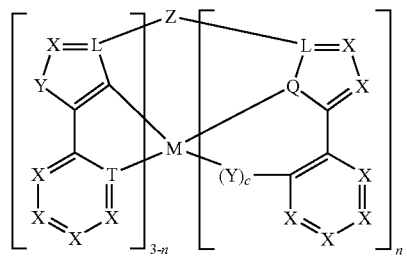
compounds (25)
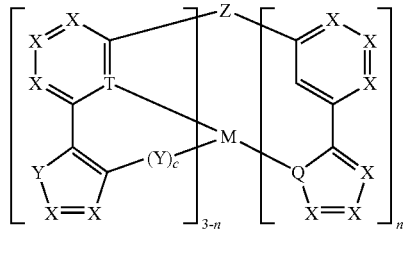
compounds (26)

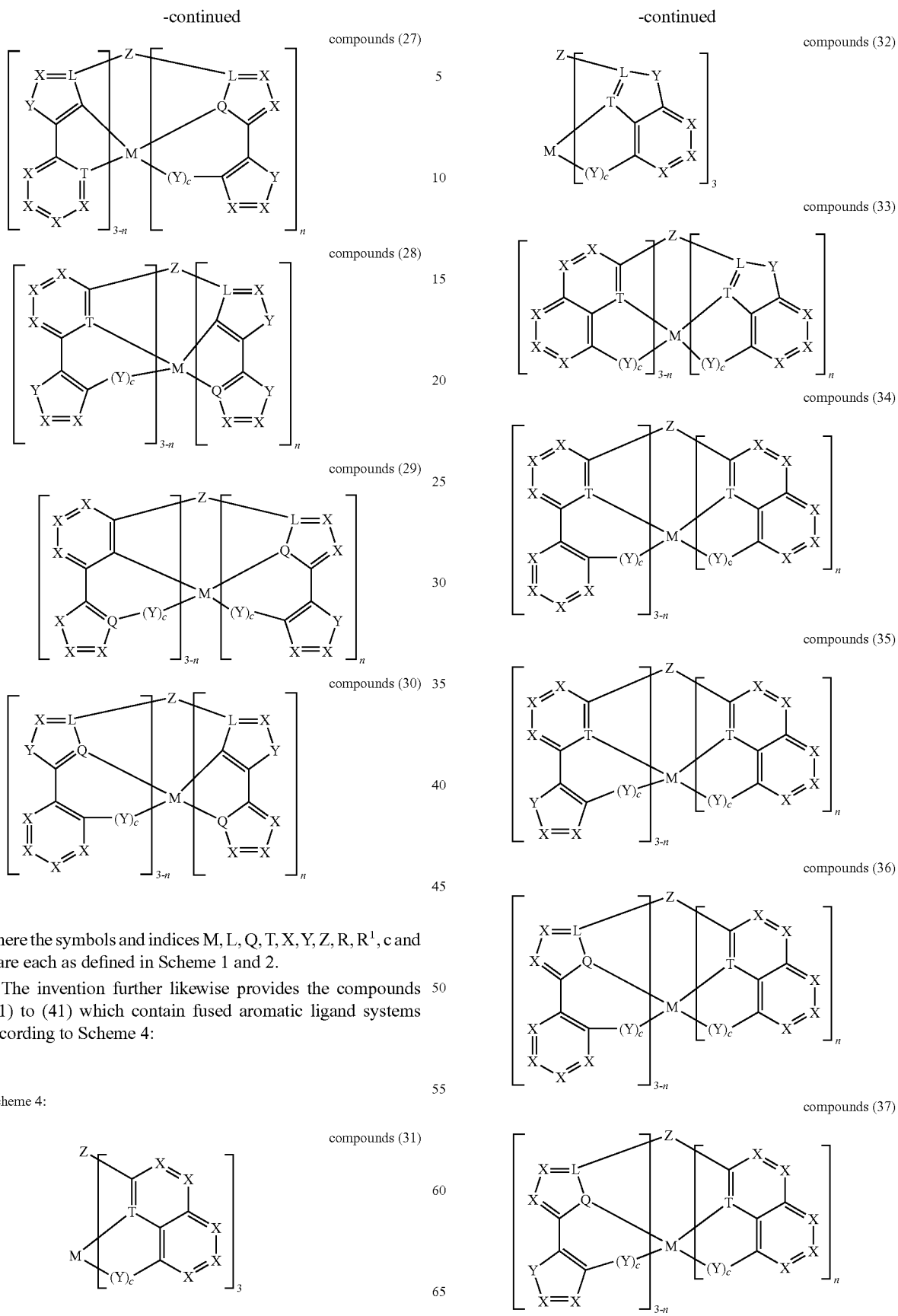
where the symbols and indices M, L, Q, T, X, Y, Z, R, R¹, c and n are each as defined in Scheme 1 and 2.
The invention further likewise provides the compounds (31) to (41) which contain fused aromatic ligand systems according to Scheme 4:
Scheme 4:

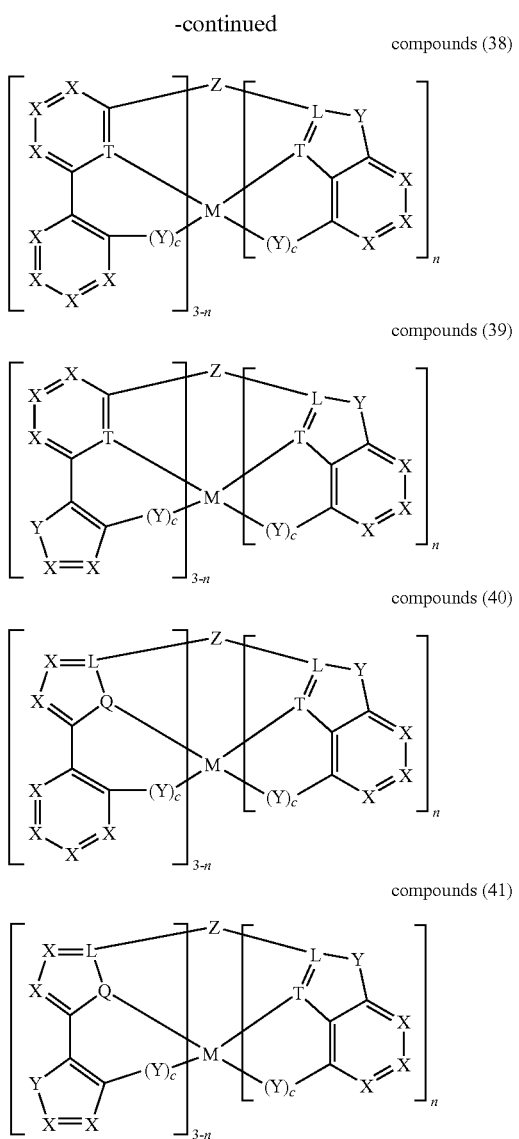

compounds (38)

compounds (39)

compounds (40)

compounds (41)

where the symbols and indices M, L, Q, T, X, Y, Z, R, $R^1$, c and n are each as defined in Scheme 1 and 2.

Preference is given to inventive compounds (1) to (41) in which the symbol M=Al, Ga, In, Sc, Y, La, Ru, Os, Rh, Ir, Au.

Preference is likewise given to inventive compounds (1) to (41) in which the symbol L=C, N.

Preference is likewise given to inventive compounds (1) to (41) in which the symbol Q=O, S.

Preference is likewise given to inventive compounds (1) to (41) in which the symbol T=N.

Preference is likewise given to inventive compounds (1) to (41) in which the symbol X=CR, N.

Preference is likewise given to inventive compounds (1) to (41) in which the symbol Z=B, CH, $CR^1$, $COR^1$, CF, CCl, CBr, SiR, N, P, PO, $RC(CR_2)_3$, $RC(CR_2CR_2)_3$, cis,cis-1,3,5-cyclohexyl, $RSi(CR_2)_3$, $RSi(CR_2CR_2)_3$, $N(CR_2)_3$, $N(C=O)_3$, $N(CR_2CR_2)_3$.

Preference is likewise given to inventive compounds (1) to (41) in which the symbol Y=O, S.

Preference is likewise given to inventive compounds (1) to (41) in which the symbol R represents H, F, Cl, Br, I, CN, a straight-chain or branched or cyclic alkyl or alkoxy group having from 1 to 6 carbon atoms or an aryl or heteroaryl group which has from 3 to 8 carbon atoms and may be substituted by one or more nonaromatic R radicals, in which a plurality of substituents R, either on the same ring or on the two different rings, together may in turn form a further mono- or polycyclic, aliphatic or aromatic ring system.

When ring systems are formed by the R radicals in the compounds (1) to (41), they are preferably benzene, 1- or 2-naphthalene, 1-, 2- or 9-anthracene, 2-, 3- or 4-pyridine, 2-, 4- or 5-pyrimidine, 2-pyrazine, 3- or 4-pyridazine, 2-, 3-, 4-, 5-, 6-, 7- or 8-quinoline, 2- or 3-pyrrole, 3-, 4- or 5-pyrazole, 2-, 4- or 5-imidazole, 2- or 3-thiophene, 2- or 3-selenophene, 2- or 3-furan, 2-(1,3,4-oxadiazole), indole or carbazole.

The present invention likewise provides the polypodal ligands according to compounds (42) to (82), according to Scheme 5:

Scheme 5:

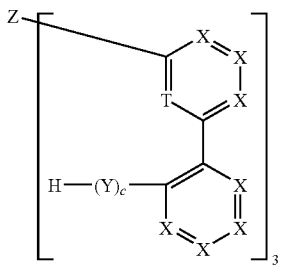

compounds (42)

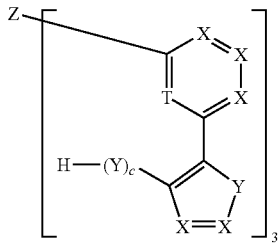

compounds (43)

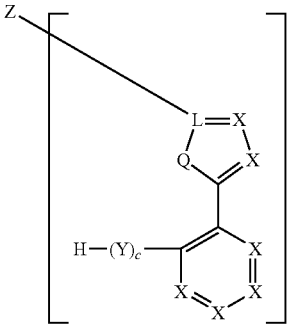

compounds (44)

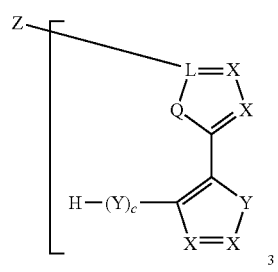

compounds (45)

compounds (46)
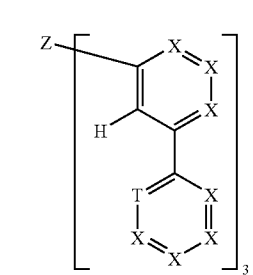
compounds (47)
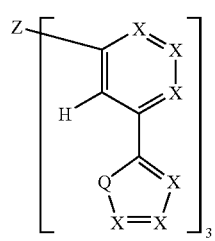
compounds (48)
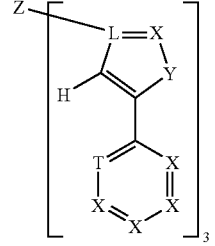
compounds (49)
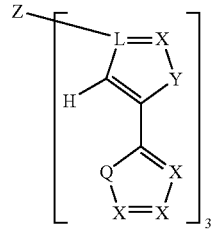
compounds (50)
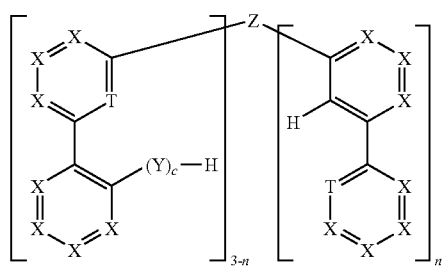
compounds (51)
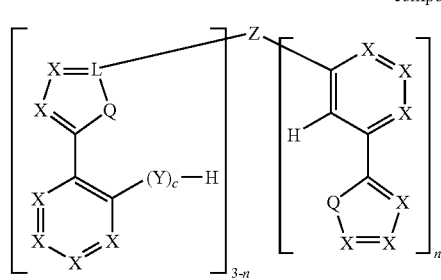
compounds (52)
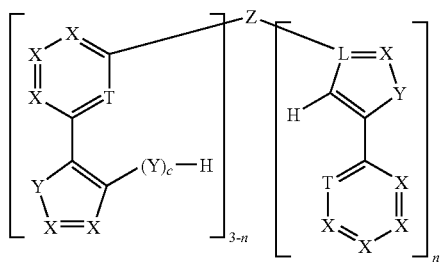
compounds (53)
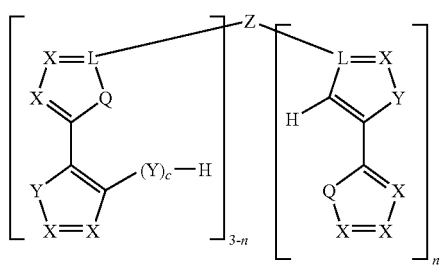
compounds (54)
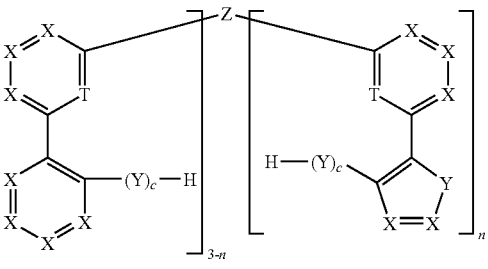
compounds (55)
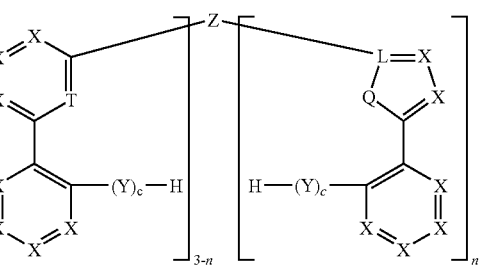
compounds (56)
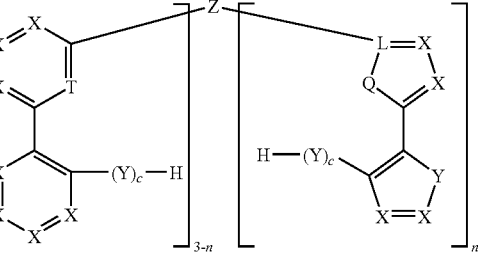

-continued
compounds (57)
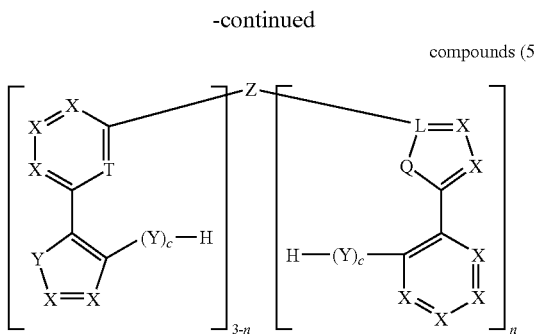
compounds (62)
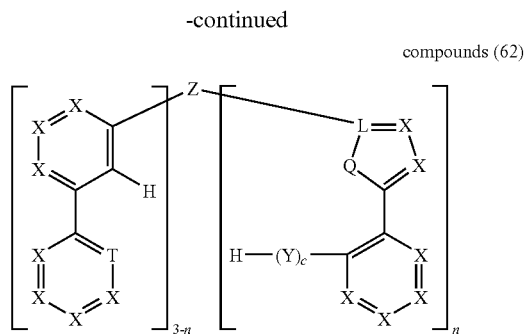
compounds (58)
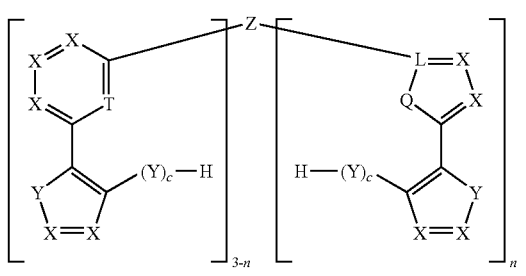
compounds (63)
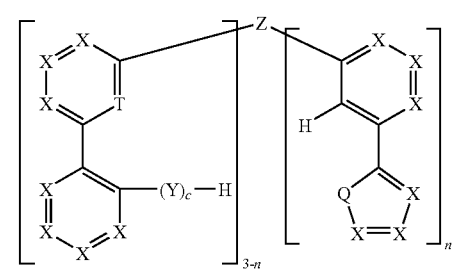
compounds (59)
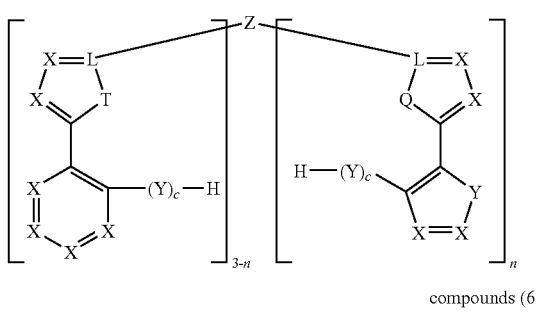
compounds (64)
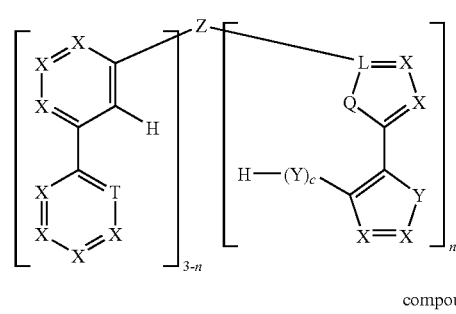
compounds (60)
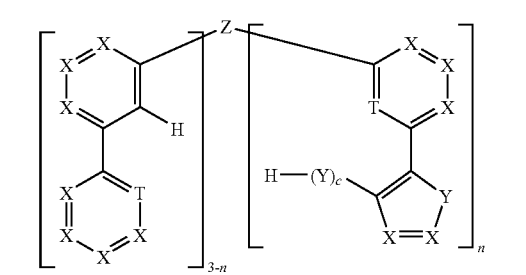
compounds (65)
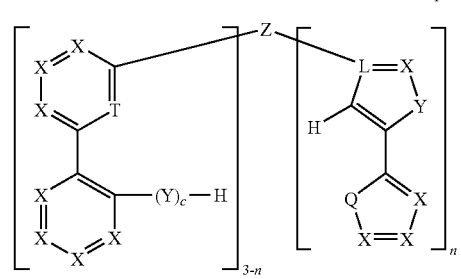
compounds (61)
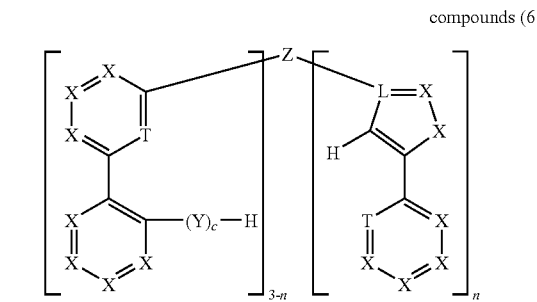
compounds (66)
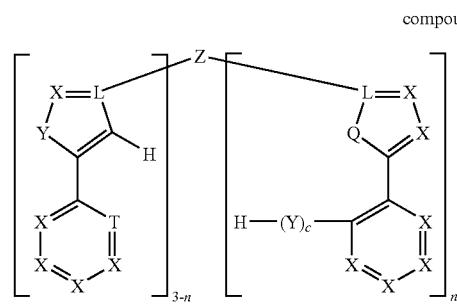

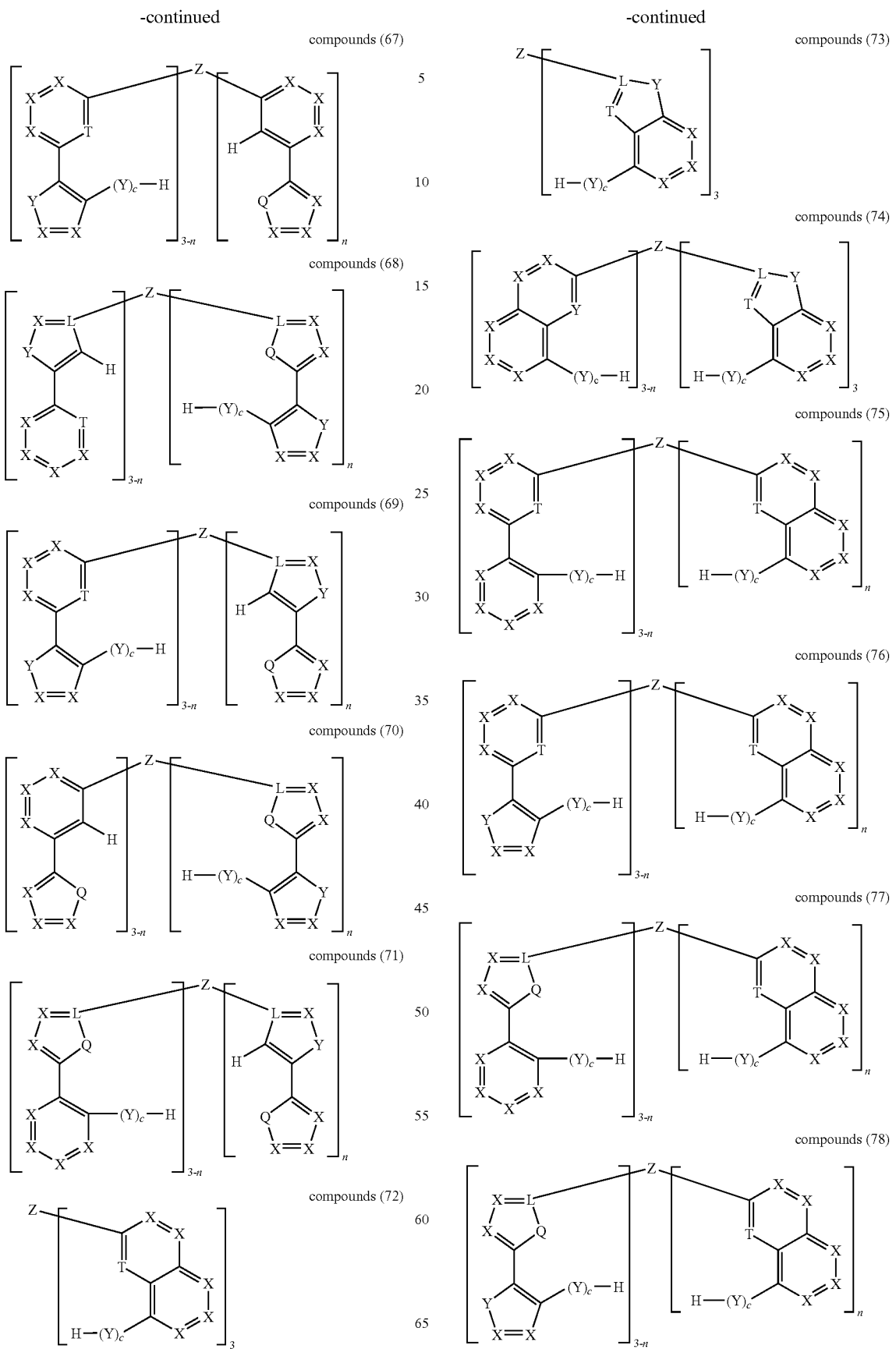

-continued compounds (79)

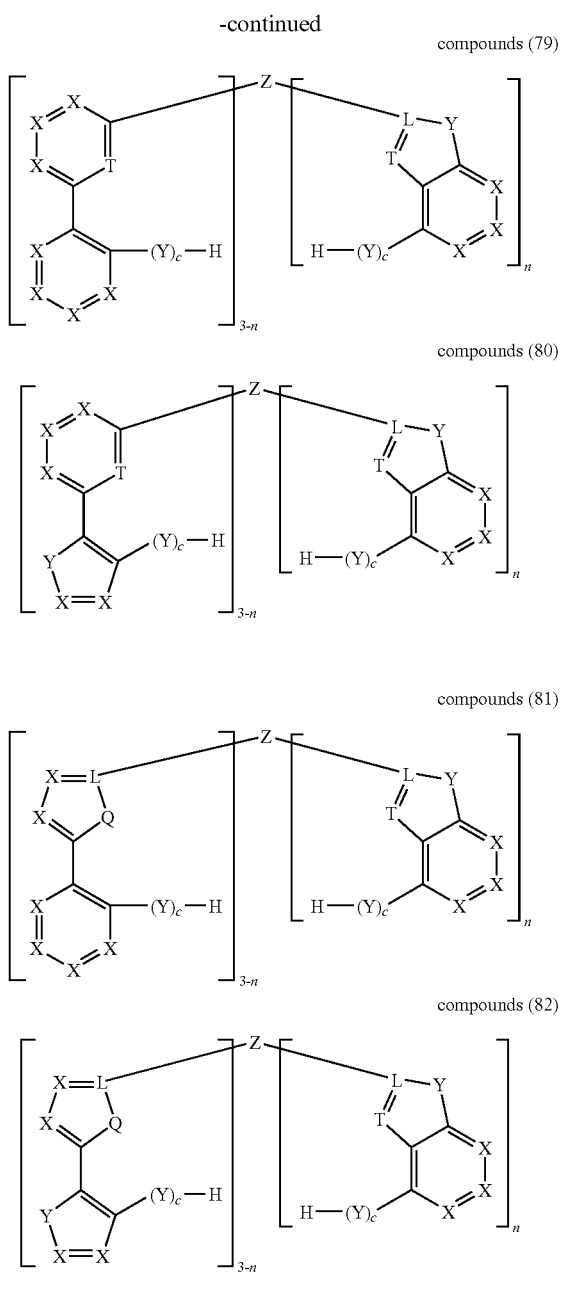

compounds (80)

compounds (81)

compounds (82)

where the symbols and indices Q, L, T, X, Y, Z, R, R$^1$, c, n are each as defined in Scheme 1 and 2.

The inventive compounds (1) to (41) can in principle be prepared by various processes, although the process described below has been found to be particularly suitable.

The present invention therefore further provides a process for preparing the compounds (1) to (41) by reacting the polypodal ligands of the compounds (42) to (82) with metal alkoxides of the formula (83), with metal ketoketonates of the formula (84) and metal halides of the formula (85), compounds (83)

M(OR$^1$)$_3$

-continued compounds (84)

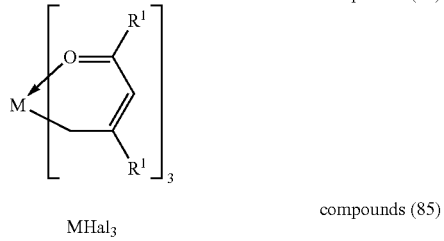

compounds (85)

MHal$_3$ where the symbol R$^1$ is as defined in Scheme 1 and Hal=F, Cl, Br, I.

This process allows the complexes to be obtained readily in high purity, preferably in a purity of >99%, by $^1$H NMR or HPLC.

The synthetic methods illustrated here allow examples including the examples of compounds (1) to (41) shown below to be prepared.

Example 1

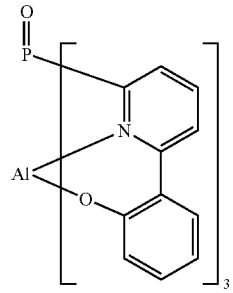

Example 2

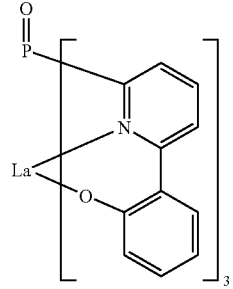

Example 3

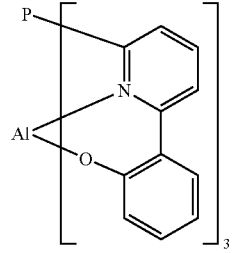

Example 4
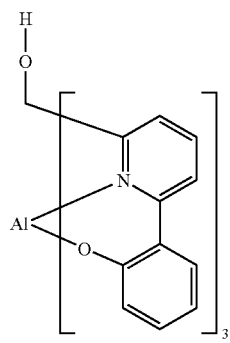
Example 5
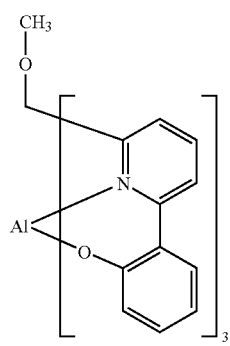
Example 6
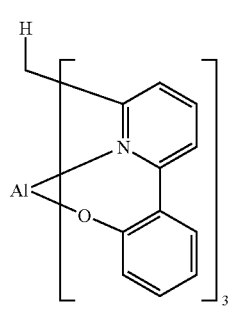
Example 7
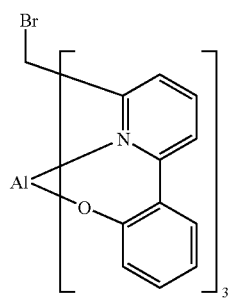
Example 8
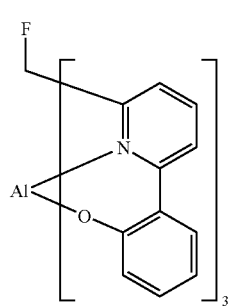
Example 9
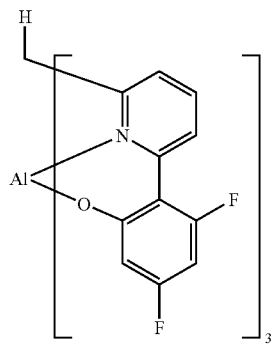
Example 10
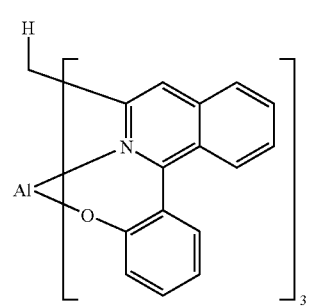
Example 11
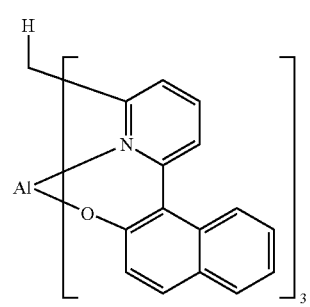
Example 12
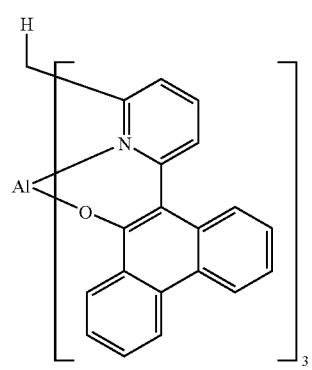

-continued
Example 13
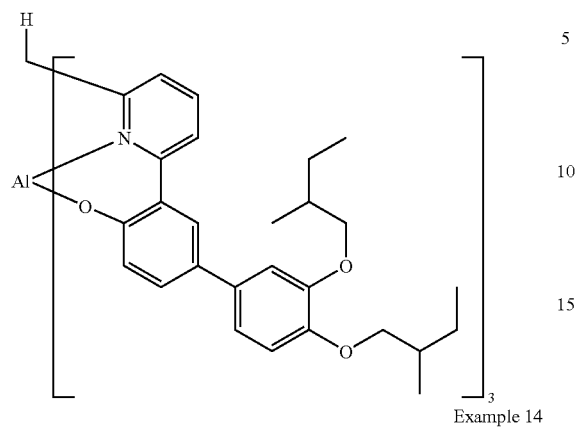
Example 14
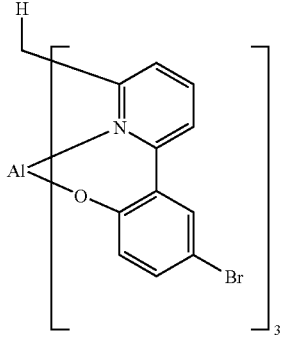
Example 15
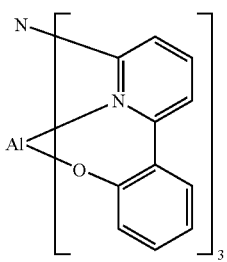
Example 16
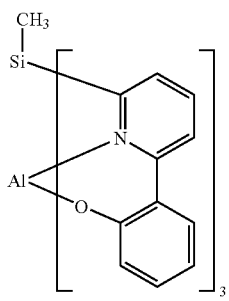
Example 17
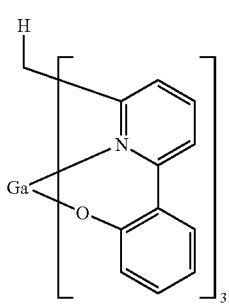
-continued
Example 18
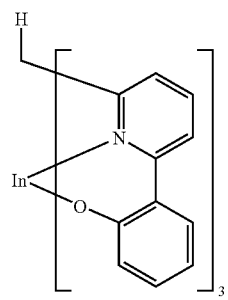
Example 19
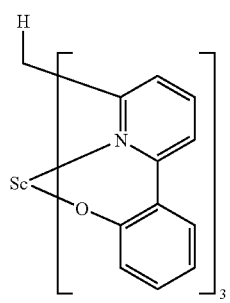
Example 20
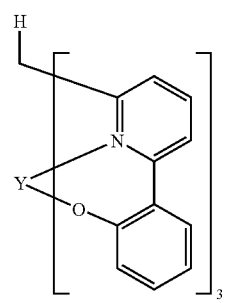
Example 21
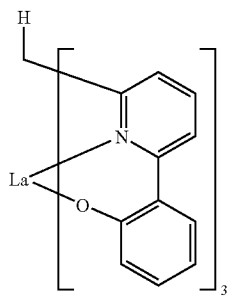
Example 22
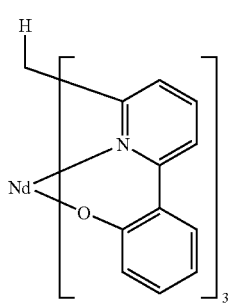

Example 23
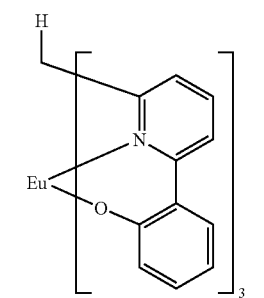
Example 24
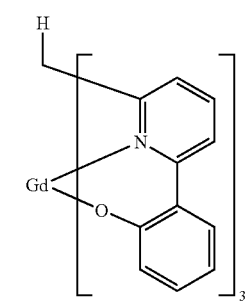
Example 25
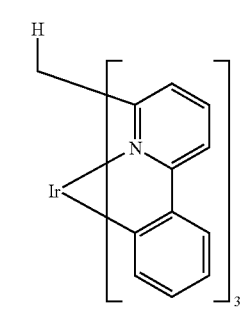
Example 26
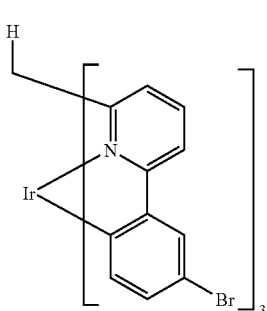
Example 27
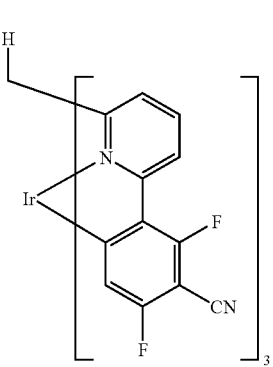
Example 28
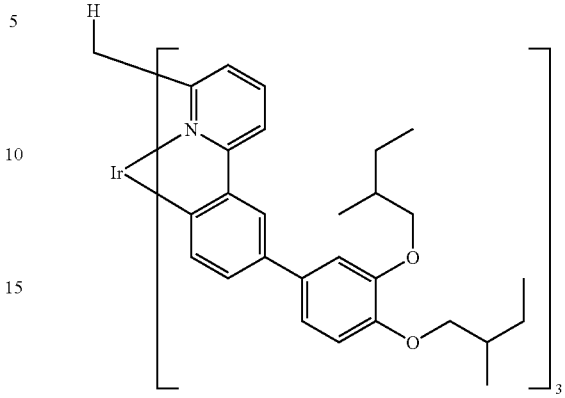
Example 29
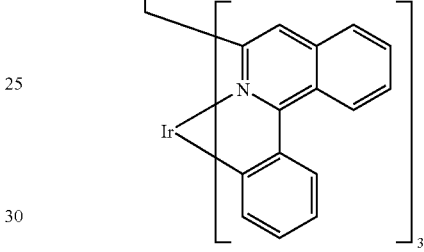
Example 30
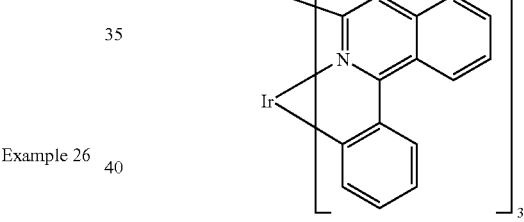
Example 31
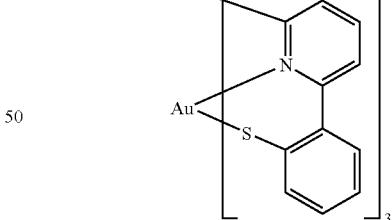
Example 32
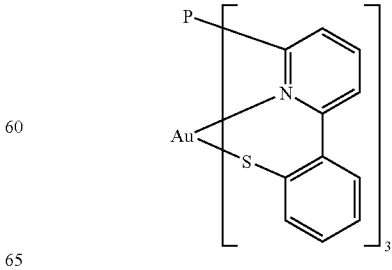

Example 33
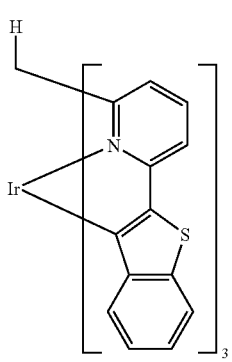
Example 34
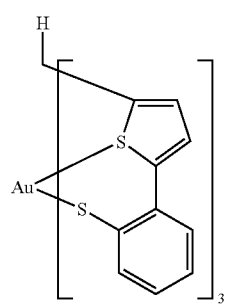
Example 35
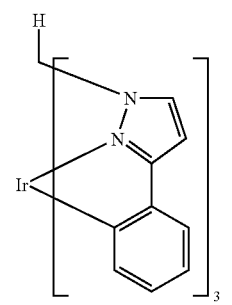
Example 36
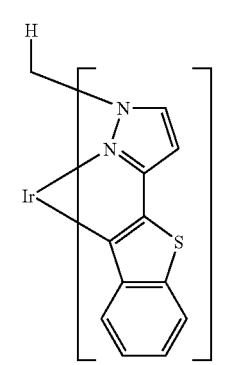
Example 37
Example 38
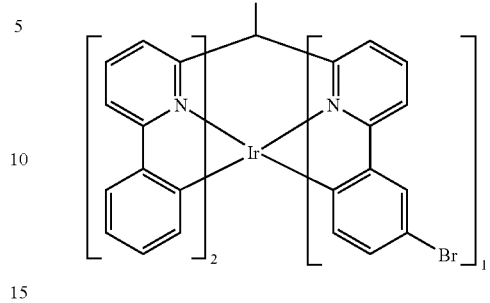
Example 39
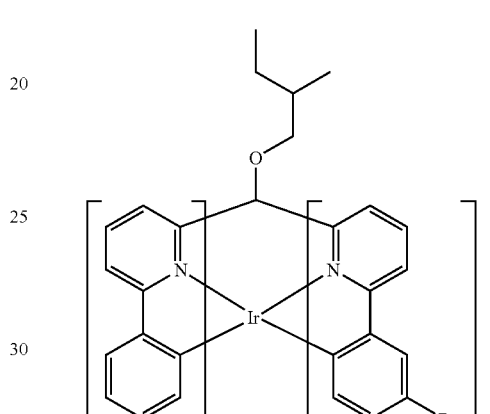
Example 40
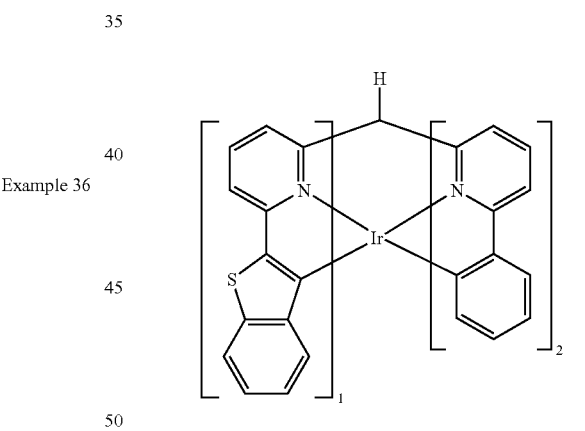
Example 41
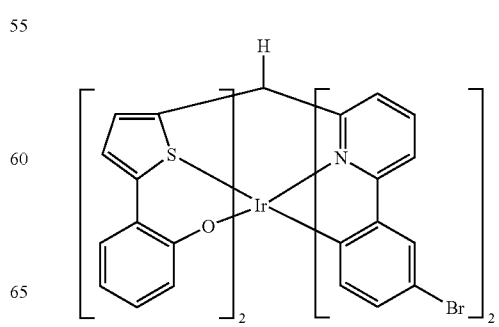

-continued
Example 42
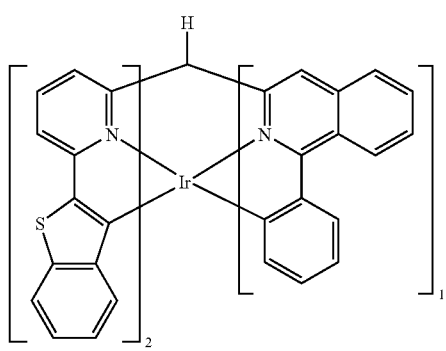
Example 43
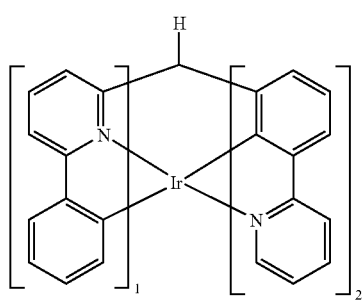
Example 44
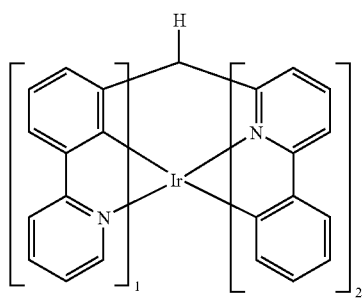
Example 45
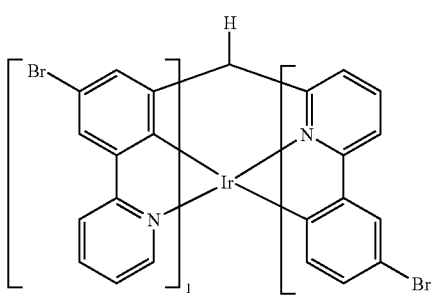
Example 46
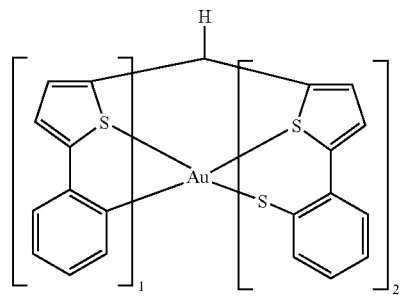
Example 47
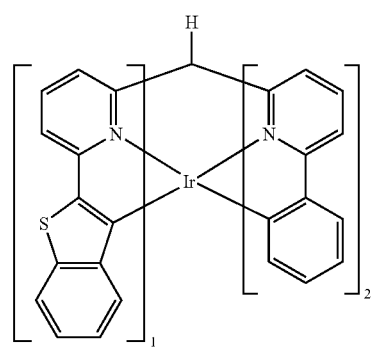
Example 48
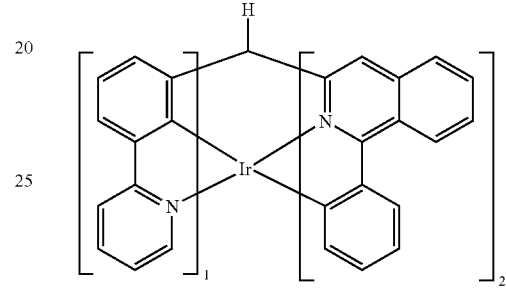
Example 49
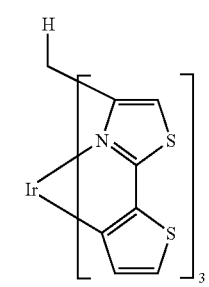
Example 50
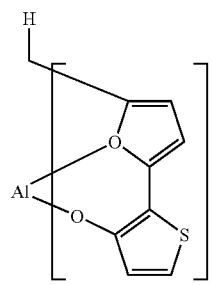
Example 51
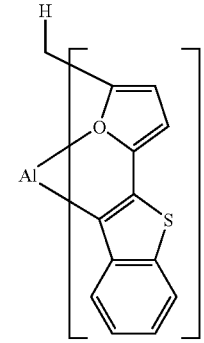

Example 52
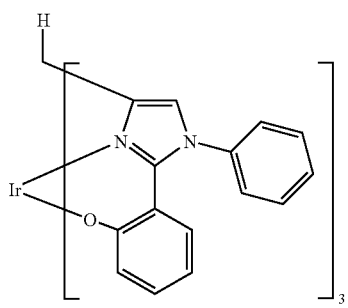
Example 53
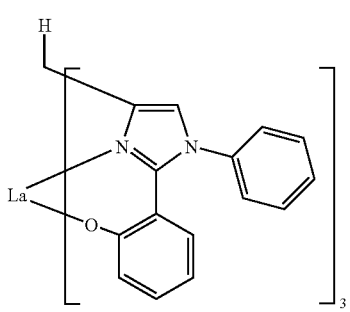
Example 54
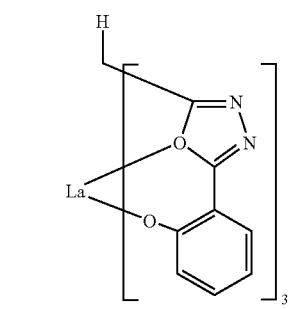
Example 55
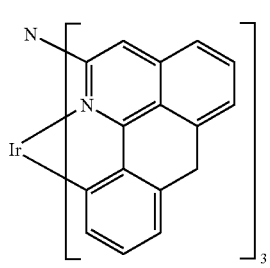
Example 56
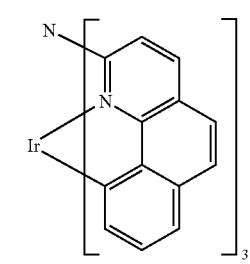
Example 57
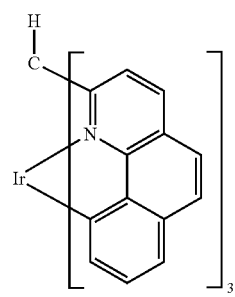
Example 58
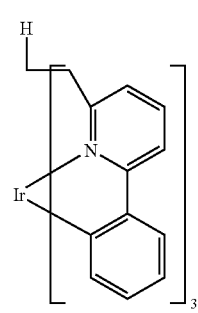
Example 59
Example 60
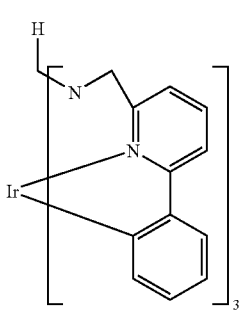
Example 61
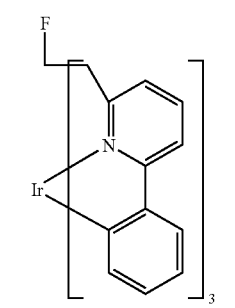

-continued
Example 62
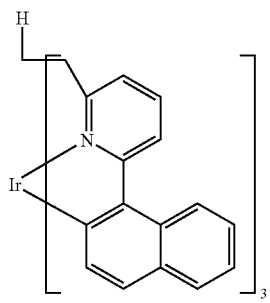
Example 63
Example 64
Example 65
-continued
Example 66
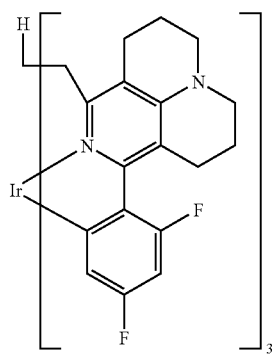
Example 67
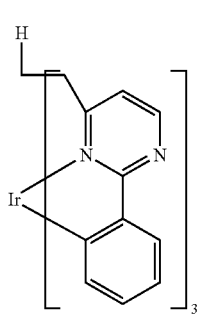
Example 68
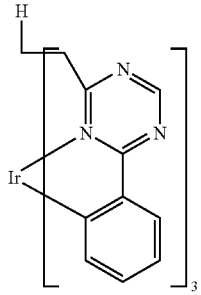
Example 69
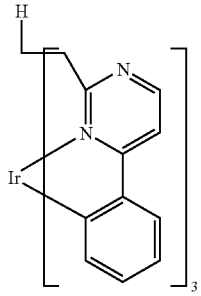
Example 70
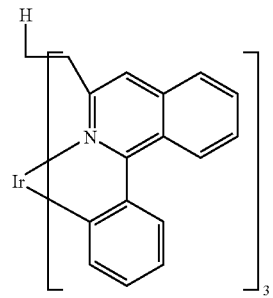

-continued
Example 71
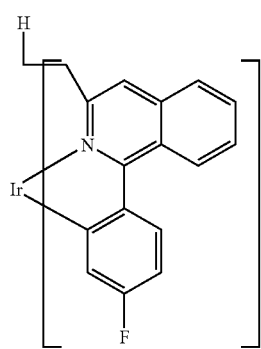
Example 72
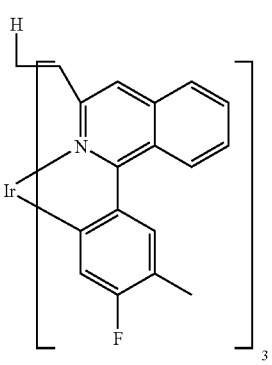
Example 73
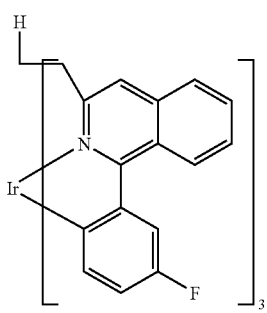
Example 74
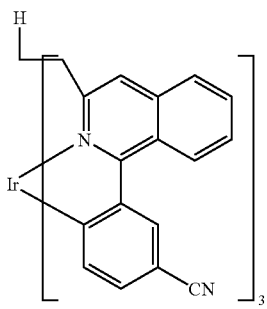
Example 75
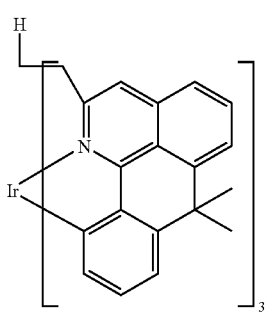
-continued
Example 76
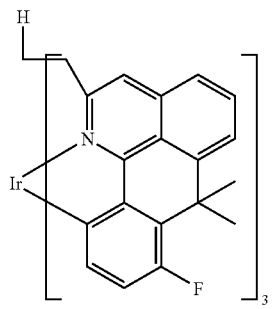
Example 77
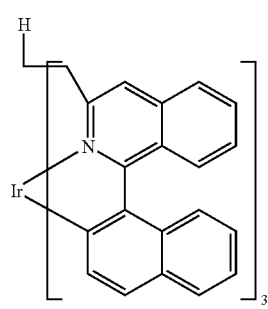
Example 78
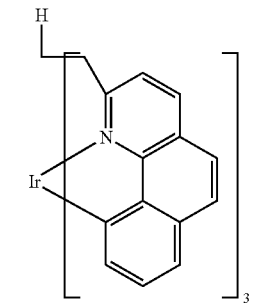
Example 79
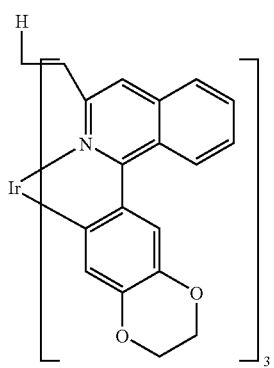

-continued
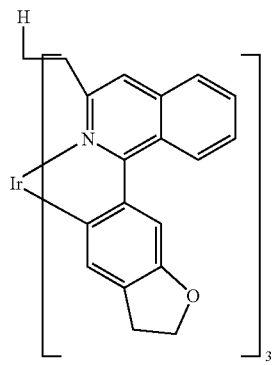
Example 80
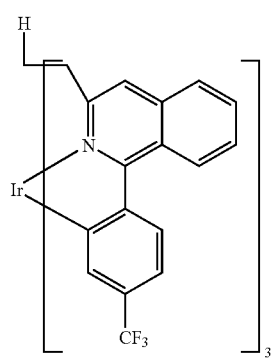
Example 81
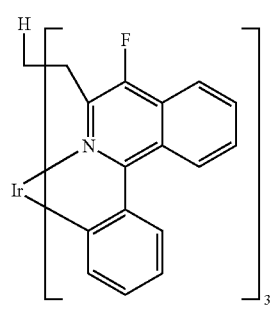
Example 82
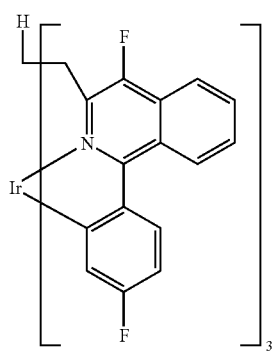
Example 83
-continued
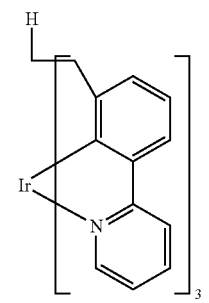
Example 84
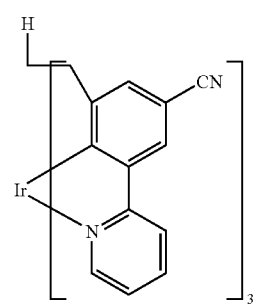
Example 85
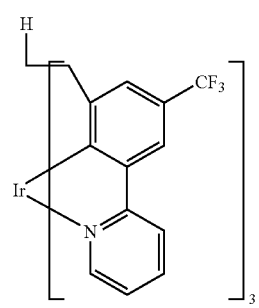
Example 86
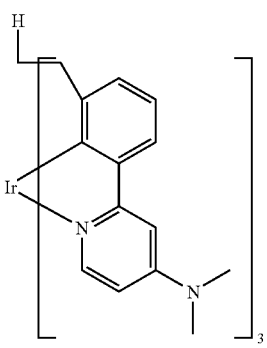
Example 87
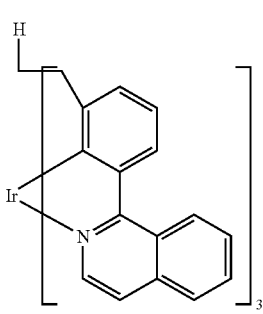
Example 88

Example 89
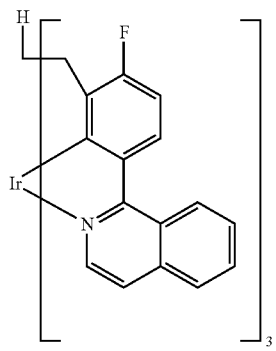
Example 90
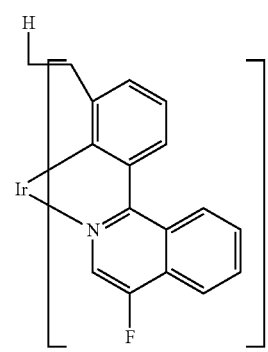
Example 91
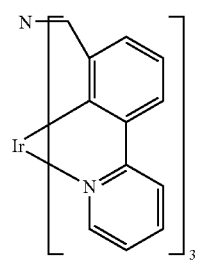
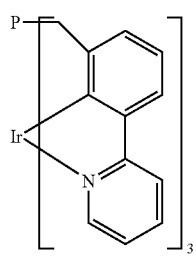
Example 93
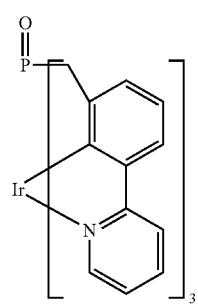
Example 94
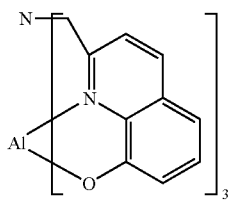
Example 95
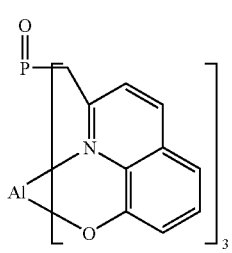
Example 96
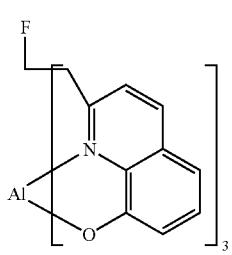
Example 97
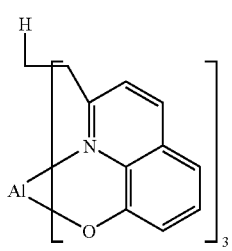
Example 98
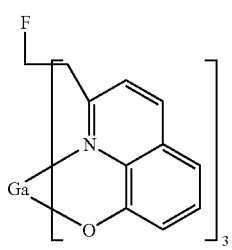
Example 99
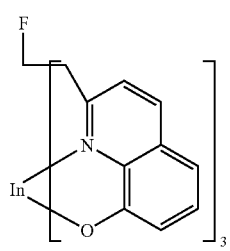

-continued

Example 100

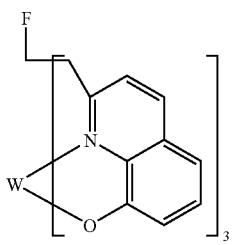

Example 101

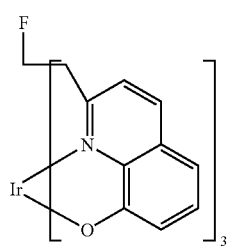

Example 102

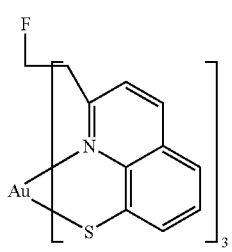

The above-described inventive compounds, for example compounds according to Examples 7, 14, 26, 27, 37, 38, 39 and 41, may find use, for example, as comonomers to obtain corresponding conjugated, semiconjugated or else nonconjugated polymers, or else as the core of dendrimers, for example compounds according to Examples 14 and 26. The appropriate polymerization is effected preferably via the halogen functionality. For instance, they can be polymerized, inter alia, into soluble polyfluorenes (for example according to EP-A-842208 or WO 00/22026), poly-spiro-bifluorenes (for example according to EP-A-707020 or EP-A-894107), poly-para-phenylenes (for example according to WO 92/18552), polycarbazoles (for example according to the applications DE 10304819.7 and DE 10328627.6), polyvinylcarbazoles or else polythiophenes (for example according to EP-A-1028136), or else copolymers of a plurality of these units.

The invention thus further provides conjugated, semiconjugated and nonconjugated polymers or dendrimers containing one or more compounds of the formula (1) to (41), in which one or more of the above-defined R radicals is a bond to the polymer or dendrimer.

In addition, the inventive metal complexes may of course also be functionalized further and thus be converted to extended metal complexes. Here, mention may be made as an example of the functionalization with arylboronic acids according to SUZUKI or with amines according to HARTWIG-BUCHWALD.

The above-described inventive compounds, polymers, dendrimers or, as described above, compounds which have been further functionalized find use as active components in electronic components, for example organic light-emitting diodes (OLEDs), organic integrated circuits (O-ICs), organic field-effect transistors (OFETs), organic thin-film transistors (OTFTs), organic solar cells (O-SCs) or organic laser diodes (O-lasers).

Active components are, for example, charge injection or charge transport materials, charge blocking materials and emission materials. For this function, the inventive compounds exhibit particularly good properties, as has already been illustrated above and will be further explained below in more detail.

The invention thus further provides for the use of these compounds in electronic components.

The invention further provides electronic components, for example organic integrated circuits (O-ICs), organic field-effect transistors (OFETs), organic thin-film transistors (OTFTs), organic solar cells (O-SCs) or organic laser diodes (O-lasers), but in particular organic light-emitting diodes (OLEDs) which comprise one or more of the inventive compounds, polymers or dendrimers.

The present invention is illustrated in detail by the examples which follow of charge transport and hole blocker materials, without any intention to restrict it thereto. Without inventive activity, those skilled in the art can use the remarks to prepare further inventive complexes, for example emission materials, or employ the process according to the invention.

EXAMPLES

Synthesis of Homoleptic Aluminum, Iron and Lanthanum Chelate Complexes with Hexapodal Ligands Unless stated otherwise, the syntheses which follow were carried out under a protective gas atmosphere in dried solvents. The reactants were purchased from ALDRICH or ABCR [2-methoxybenzeneboronic acid, 2-bromo-4-fluorophenol, 2-bromo-5-fluorophenol, potassium fluoride (spray-dried), diethylaminosulfur trifluoride (DAST), tri-tert-butylphosphine, palladium(II) acetate, pyridinium hydrochloride, aluminum triisopropoxide, 10% by weight solution of tris(2-methoxyethanolato)lanthanum(III) in 2-methoxyethanol]. Tris(2-bromo-6-pyridyl)phosphine and tris(2-bromo-6-pyridyl)methanol were prepared as described in WO 98/22148.

Example 1

Tris(2-bromo-6-pyridyl)phosphine oxide

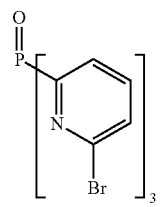

A suspension, heated to boiling, of 50.2 g (100.0 mmol) of tris(2-bromo-6-pyridyl)phosphine in 500 ml of chloroform was admixed with intensive stirring dropwise with a mixture of 11 ml of 35% by weight $H_2O_2$ and 50 ml of water, which afforded a clear solution. After stirring under reflux for 5 h, the solution was allowed to cool to room temperature. The solution was washed with 500 ml of water, and the organic phase was removed and concentrated to 50 ml under reduced pressure. After standing for 2 h, the precipitated crystals were filtered off, washed three times with 100 ml of n-hexane and then dried at 70° C. under reduced pressure. The yield at a purity of 99.0% was 47.1 g (90.9%).

$^1$H NMR (CDCl$_3$) δ [ppm]=8.14 (ddd, $^3J_{HP}$=5.4 Hz, $^3J_{HH}$=7.8 Hz, $^4J_{HH}$=1.0 Hz, 3H, H-3), 7.69 (ddd, $^4J_{HP}$=4.6 Hz, $^3J_{HH}$=7.9 Hz, $^3J_{HH}$=7.9 Hz, 3H, H-4), 7.61 (ddd, $^5J_{HP}$=2.1 Hz, $^3J_{HH}$=7.9 Hz, $^4J_{HH}$=1.0 Hz, 3H, H-5).

$^{31}$P{$^1$H} NMR (CDCl$_3$) δ [ppm]=11.8 (s).

Example 2

Tris(6-(2-methoxyphenyl)-2-pyridyl)phosphine oxide

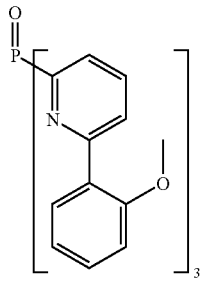

An efficiently stirred suspension of 38.8 g (75.0 mmol) of tris(2-bromo-6-pyridyl)phosphine oxide, 51.3 g (337.5 mmol) of 2-methoxybenzeneboronic acid and 43.1 g (742.5 mmol) of potassium fluoride in 750 ml of anhydrous THF was admixed with 593 mg (2.93 mmol) of tri-tert-butylphosphine and then with 505 mg (2.25 mmol) of palladium(II) acetate, and subsequently heated under reflux for 16 h. After cooling, the reaction mixture was admixed with 1500 ml of ethyl acetate and 1000 ml of water. The organic phase was removed, washed twice with 500 ml of water and once with 500 ml of sat. sodium chloride solution, and subsequently dried over magnesium sulfate. After the organic phase had been concentrated under reduced pressure (end pressure 1 mbar, temperature 90° C.), 44.3 g (98.5%) of a pale yellow highly viscous oil remained, which was reacted further without purification.

$^1$H NMR (CDCl$_3$) δ [ppm]=8.14 (ddd, 3H), 8.02 (ddd, 3H), 7.85 (dd, 3H), 7.76 (ddd, 3H), 7.30 (ddd, 3H), 6.94 (dd, 3H), 6.87 (ddd, 3H), 3.10 (s, 9H CH$_3$).

$^{31}$P{H} NMR (CDCl$_3$): δ [ppm]=14.0 (s).

Example 3

Tris(6-(2-hydroxyphenyl)-2-pyridyl)phosphine oxide, (PPL-01)

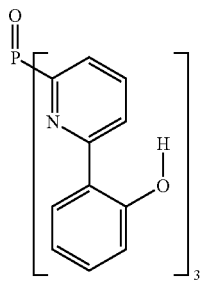

A mixture of 30.0 g (50 mmol) of tris(6-(2-methoxyphenyl)-2-pyridyl)phosphine oxide and 104.0 g (900 mmol) of pyridinium hydrochloride was stirred at 130° C. for 12 h. After the melt had been cooled to 80° C., it was admixed with 300 ml of water and then with a solution of 44.9 g (800 mmol) of potassium hydroxide in 100 ml of water. The aqueous phase was extracted three times with 500 ml of dichloromethane. The combined organic phases were washed three times with 500 ml of water. After the organic phase had been dried over magnesium sulfate and the dichloromethane had been removed, the oily residue was taken up in 100 ml of methyl tert-butyl ether and admixed with 100 ml of n-heptane. After standing for 12 h, the colorless crystals were filtered off with suction and recrystallized from methyl tert-butyl ether/n-heptane. The yield was 10.9 g (39.1%) at a purity of greater than 99.0% by $^1$H NMR.

$^1$H NMR (CDCl$_3$) δ [ppm]=14.33 (s, 3H, OH), 8.45 (m, 3H), 8.13 (m, 3H), 7.88 (m, 3H), 7.61 (m, 3H), 7.23 (m, 3H), 7.01 (m, 3H), 6.90 (m, 3H).

$^{31}$P{$^1$H} NMR (CDCl$_3$) δ [ppm]=10.3 (s).

Example 4

Tris(2-bromo-6-pyridyl)fluoromethane

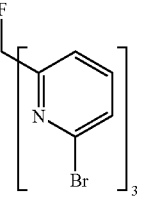

A solution of 50.0 g (100 mmol) of tris(2-bromo-6-pyridyl) methanol in 750 ml of dichloromethane was admixed with good stirring dropwise with 47.3 ml (400 mmol) of diethylaminosulfur trifluoride. Subsequently, the reaction mixture was heated under reflux for 30 min, then cooled to 5° C., and admixed with good stirring (highly exothermic!!!) with 300 ml of water and then with a solution of 64.0 g (1600 mmol) of sodium hydroxide in 600 ml of water (highly exothermic!!!). The organic phase was removed, the aqueous phase was washed twice with 200 ml of dichloromethane, and the combined organic phases were dried over calcium chloride and subsequently freed of dichloromethane. The remaining red-brown crystal slurry was taken up in 100 ml of methanol and filtered off. After washing with methanol, the colorless to beige crystals were dried under reduced pressure. The yield was 47.4 g (91.3%) at a purity of greater than 99.0% by $^1$H NMR.

$^1$H NMR (CDCl$_3$): δ [ppm]=7.58 (ddd, $^3J_{HH}$=7.7 Hz, $^3J_{HH}$=7.7 Hz, $^5J_{FH}$=0.7 Hz, 1H, H-4), 7.53 (dd, $^3J_{HH}$=7.7 Hz, $^4J_{HH}$=0.7 Hz, 1H, H-3), 7.45 (ddd, $^3J_{HH}$=7.7 Hz, $^4J_{HH}$=0.7 Hz, $^4J_{FH}$=0.9 Hz, 1H, H-5).

$^{19}$F{$^1$H} NMR (CDCl$_3$) δ [ppm]=−146.2 (s).

Example 5

2-Bromo-4-fluoro-1-(tetrahydropyran-2-yloxy)benzene

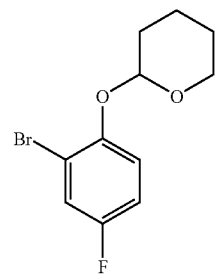

A mixture of 478.0 ml (5.24 mol) of 3,4-dihydropyran and 750 ml of dichloromethane was admixed with 65.4 g (260 mmol) of pyridinium p-toluenesulfonate. Subsequently, a solution of 500.0 g (2.62 mmol) of 2-bromo-4-fluorophenol in 500 ml of dichloromethane was added dropwise. After stirring for 24 h, the reaction mixture was admixed with a solution of 50 g of potassium carbonate in 500 ml of water, and then with 500 ml of saturated sodium chloride solution. The organic phase was removed, dried over potassium carbonate and, after freeing it of the solvent and potassium carbonate, fractionally distilled (approx. 1 mbar, top temperature from 79 to 82° C.) by means of a Vigreux column (40 cm). The product was obtained as a colorless, low-viscosity oil. The yield was 520.5 g (72.2%) at a purity of greater than 98.0% by $^1$H NMR.

$^1$H NMR (CDCl$_3$): δ [ppm]=7.27 (dd, $^3J_{FH}$=8.0 Hz, $^4J_{HH}$=3.0 Hz, 1H, H-3), 7.10 (dd, $^3J_{HH}$=9.7 Hz, $^4J_{FH}$=5.0 Hz, 1H, H-6), 6.93 (ddd, $^3J_{HH}$=9.7 Hz, $^3J_{FH}$=8.0 Hz, $^4J_{HH}$=3.2 Hz, 1H, H-5), 5.39 (m, 1H, CH), 3.88 (m, 1H, CH$_2$O), 3.59 (m, 1H, CH$_2$O), 2.12-1.53 (m, 6H, CH$_2$).

$^{19}$F{$^1$H} NMR (CDCl$_3$): δ [ppm]=−121.1 (s).

Example 6

5-Fluoro-2-(tetrahydropyran-2-yloxy)benzeneboronic acid

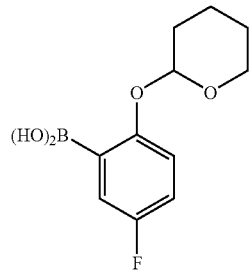

48.6 g (2.00 mol) of magnesium and 510 g (1.85 mol) of 2-bromo-4-fluoro-1-(tetrahydropyran-2-yloxy)benzene in 1250 ml of THF were used to prepare a Grignard reagent. This Grignard reagent was slowly added dropwise at −78° C. to a mixture of 241.6 ml (2.00 mol) of trimethyl borate in 500 ml of THF. On completion of addition, the reaction mixture was allowed to warm to room temperature and was hydrolyzed by addition of 100 ml of saturated potassium carbonate solution and 1000 ml of water. The organic phase was washed with saturated sodium chloride, solution. (1×500 ml) and subsequently concentrated to dryness. The yield was 428.2 g (1.78 mol), and the product was obtained as a waxy solid which contained varying proportions of boronic anhydride and borinic acids and was used in the following stage without further purification.

Example 7

Tris(6-(5-fluoro-2-hydroxyphenyl)-2-pyridyl]fluoromethane, (PPL-02)

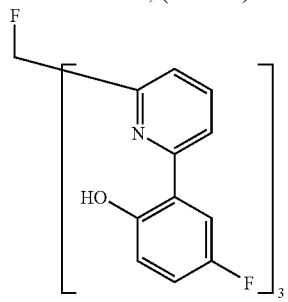

Procedure of the Suzuki coupling analogous to Example 2, for which 51.9 g (100 mmol) of tris(2-bromo-6-pyridyl)fluoromethane (Example 4), 108.0 g (450 mmol) of 5-fluoro-2-(tetrahydropyran-2-yloxy)benzeneboronic acid (Example 6), 57.5 g (990 mmol) of potassium fluoride, 1.35 g (6 mmol) of palladium(II) acetate and 1.8 ml (8 mmol) of tri-tert-butylphosphine in 1000 ml of THF were used.

After 6 h under reflux, the reaction mixture was freed of the THF on a rotary evaporator, and the slurrylike residue was taken up in 1000 ml of methanol, admixed with a mixture of 300 ml of water and 55 ml of 5N HCl and subsequently stirred at 50° C. for a further 3 h. The resulting crystal slurry was filtered off with suction (P3), washed with methanol and dried. Recrystallization from a little chloroform with addition of methanol gave 53.2 g (89.0%) of the product in the form of colorless crystals having a purity of greater than 99.0% by $^1$H NMR.

$^1$H NMR (CDCl$_3$): δ [ppm]=12.34 (s, 3H, OH), 7.99 (dd, $^3J_{HH}$=8.4 Hz, $^3J_{HH}$=8.4 Hz, 3H, H-4-Py), 7.86 (d, $^3J_{HH}$=8.4 Hz, 3H, H-5-Py), 7.79 (d, $^3J_{HH}$=8.4 Hz, 3H, H-3-Py), 7.45 (dd, $^3J_{HH}$=9.4 Hz, $^4J_{FH}$=3.0 Hz, 3H, H-3), 6.95 (ddd, $^3J_{HH}$=9.4 Hz, $^3J_{FH}$=8.0 Hz, $^4J_{HH}$=3.0 Hz, 3H, H-4), 6.76 (dd, $^3J_{FH}$=9.0 Hz, $^4J_{HH}$=3.0 Hz, 3H, H-6).

$^{19}$F{$^1$H} NMR (CDCl$_3$): δ [ppm]=−144.9 (s, 1F), −125.9 (s, 3F).

Example 8

2-Bromo-5-fluoro-1-(tetrahydropyran-2-yloxy)benzene

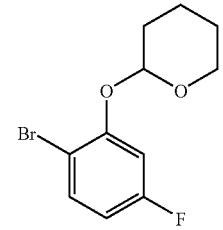

Procedure analogous to Example 5. Use of 478.0 ml (5.24 mol) of 3,4-dihydropyran, 65.4 g (260 mmol) of pyridinium p-toluenesulfonate and 500.0 g (2.62 mmol) of 2-bromo-5-fluorophenol. The yield was 562.2 g (78.0%) at a purity of greater than 98.0% by $^1$H NMR.

$^1$H NMR (CDCl$_3$): δ [ppm]=7.45 (dd, $^3J_{HH}$=9.1 Hz, $^4J_{FH}$=6.4 Hz, 1H, H-3), 6.92 (dd, $^3J_{FH}$=10.7 Hz, $^4J_{FH}$=2.7 Hz, 1H, H-6), 6.60 (ddd, $^3J_{HH}$=9.1 Hz, $^3J_{FH}$=8.7 Hz, $^4J_{HH}$=2.7 Hz, 1H, H-4), 5.46 (m, 1H, CH), 3.84 (m, 1H, CH$_2$O), 3.62 (m, 1H, CH$_2$O), 2.14-1.56 (m, 6H, CH$_2$).

$^{19}$F{$^1$H} NMR (CDCl$_3$) δ [ppm]=−112.7 (s).

Example 9

4-Fluoro-2-(tetrahydropyran-2-yloxy)benzeneboronic acid

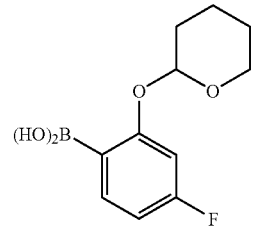

Procedure analogous to Example 6. Use of 48.6 g (2.00 mol) of magnesium, 510 g (1.85 mol) of 2-bromo-5-fluoro- 1-(tetrahydropyran-2-yloxy)benzene and 241.6 ml (2.00 mol) of trimethyl borate. The yield was 434.5 g (1.81 mol), and the product was obtained as a waxy solid which contained varying proportions of boronic anhydrides and borinic acids and was used in the following stage without further purification.

Example 10

Tris(6-(4-fluoro-2-hydroxyphenyl)-2-pyridyl)fluoromethane, (PPL-03)

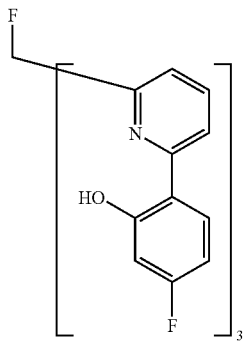

Procedure analogous to Example 7. Use of 51.9 g (100 mmol) of tris(2-bromo-6-pyridyl)fluoromethane (Example 4), 108.0 g (450 mmol) of 4-fluoro-2-(tetrahydropyran-2-yloxy)benzeneboronic acid (Example 9), 57.5 g (990 mmol) of potassium fluoride, 1.35 g (6 mmol) of palladium(II) acetate and 1.8 ml (8 mmol) of tri-tert-butylphosphine. The yield was 56.9 g (95.5%) of the product in the form of colorless crystals having a purity of greater than 99.0% by $^1$H NMR.

$^1$H NMR (CDCl$_3$): δ [ppm]=13.01 (s, 3H, OH), 7.96 (dd, $^3J_{HH}$=8.2 Hz, $^3J_{HH}$=8.2 Hz, 3H, H-4-Py), 7.86 (d, $^3J_{HH}$=8.2 Hz, 3H, H-5-Py), 7.75 (dd, $^3J_{HH}$=9.4 Hz, $^4J_{FH}$=6.4 Hz, 3H, H-6), 7.52 (d, $^3J_{HH}$=8.2 Hz, 3H, H-3-Py), 6.59 (ddd, $^3J_{HH}$=9.4 Hz, $^3J_{FH}$=8.0 Hz, $^4J_{HH}$=2.7 Hz, 3H, H-5), 6.51 (dd, $^3J_{FH}$=10.7 Hz, $^4J_{HH}$=2.7 Hz, 3H, H-3).

$^{19}$F{$^1$H} NMR (CDCl$_3$) δ [ppm]=−144.7 (s, 1F), −108.6 (s, 3F).

Example 11

Mono[tris(6-(2-oxyphenyl)-2-pyridyl)phosphinoxido]aluminum(III); Al—PPL-01

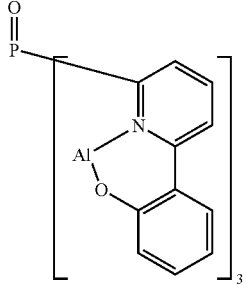

A solution of 5.58 g (10 mmol) of tris(6-(2-hydroxyphenyl)-2-pyridyl)phosphine oxide (Example 3) in 100 ml of toluene was admixed at 80° C. over 30 min with a solution of 2.04 g (10 mmol) of tris(isopropanolato)aluminum(III) in 50 ml of toluene. The reaction mixture was heated under reflux for a further 3 h. After cooling to room temperature, the colorless precipitate was filtered off with suction, washed with toluene (1×25 ml) and dried. Repeated recrystallization from DMSO gave 5.03 g (86.5%) of the complex at a purity of 99.8% by HPLC.

MS (FAB): m/e=582.

Example 12

Mono[tris(6-(2-oxyphenyl)-2-pyridyl)phosphinoxido]lanthanum(III); La—PPL-01

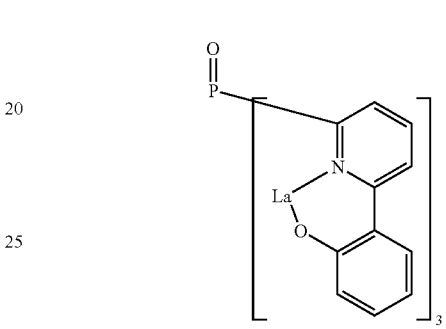

A solution of 5.58 g (10 mmol) of tris(6-(2-hydroxyphenyl)-2-pyridyl)phosphine oxide (Example 3) in 100 ml of toluene was admixed at 80° C. over 30 min with 36.4 ml (10 mmol) of a 10% by weight solution of tris(2-methoxyethanolato)lanthanum(III) in 2-methoxyethanol. The reaction mixture was heated under reflux for a further 3 h. After cooling to room temperature, the colorless precipitate was filtered off with suction, washed with toluene (1×25 ml) and dried. Repeated recrystallization from DMSO gave 5.68 g (81.7%) of the complex at a purity of 99.8% by HPLC.

MS (FAB): m/e=693.

Example 13

Mono[tris(6-(5-fluoro-2-oxyphenyl)-2-pyridyl)fluoromethanato]aluminum(III); Al—PPL-02

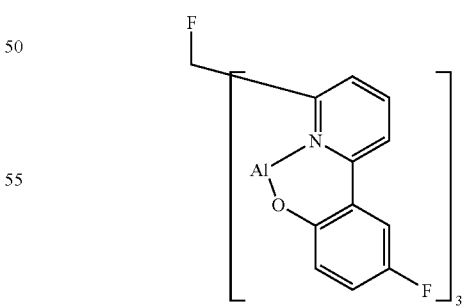

A solution of 5.96 g (10 mmol) of tris(6-(5-fluoro-2-hydroxyphenyl)-2-pyridyl)fluoromethane (Example 7) in 200 ml of THF was admixed first with 19.4 ml (240 mmol) of pyridine and then, dropwise at room temperature over 30 min, with a solution of 20 ml of 0.5 N aluminum chloride solution in ethanol. The reaction mixture was heated to reflux for a further 3 h. After cooling to room temperature, the colorless precipitate was filtered off with suction, washed with THF (3×50 ml) and ethanol (3×50 ml) and then dried. Repeated recrystallization from DMSO (200 ml) gave 5.59 g (90.3%) of the pale yellow complex at a purity of 99.9% by $^1$H NMR.

$^1$H NMR (DMSO-d6) δ[ppm]=8.23 (dd, $^3J_{HH}$=8.0 Hz, $^3J_{HH}$=8.0 Hz, 3H, H-4-Py), 8.17 (d, $^3J_{HH}$=8.0 Hz, 3H, H-5-Py), 7.99 (dd, $^3J_{HH}$=8.0 Hz, $^4J_{FH}$=3.4 Hz, 3H, H-3-Py), 7.69 (dd, $^3J_{HH}$=9.0 Hz, $^4J_{FH}$=3.0 Hz, 3H, H-3), 7.03 (ddd, $^3J_{HH}$=9.0 Hz, $^3J_{HH}$=9.0 Hz, $^4J_{FH}$=3.4 Hz, 3H, H-4), 6.19 (dd, $^3J_{FH}$=9.0 Hz, $^4J_{HH}$=3.4 Hz, 3H, H-6).

$^{19}$F{$^1$H} NMR (DMSO-d6): δ [ppm]=−177.5 (s, 1F), −128.6 (s, 3F).

$T_g$: 178° C.

Example 14

Mono[tris(6-(5-fluoro-2-oxyphenyl)-2-pyridyl)fluoromethanato]iron(III); Fe—PPL2

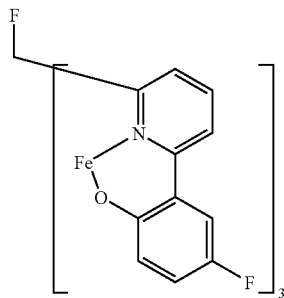

Procedure analogous to Example 13. Use of 5.96 g (10 mmol) of tris(6-(5-fluoro-2-hydroxyphenyl)-2-pyridyl)fluoromethane (Example 10) and 20 ml of a 0.5N iron(III) chloride 6H$_2$O solution in ethanol. Repeated recrystallization from DMSO (200 ml) with addition of 100 ml of ethanol after cooling of the solution to 120° C. gave 5.39 g (83.1%) of the black complex. MS (FAB): m/e=648.

Example 15

Mono[tris(6-(4-fluoro-2-oxyphenyl)-2-pyridyl)fluoromethanato]aluminum(III); Al—PPL3

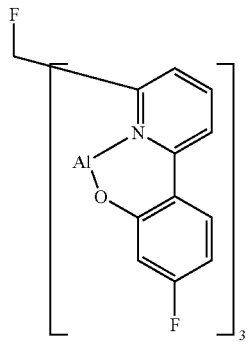

Procedure analogous to Example 13. Use of 5.96 g (10 mmol) of tris(6-(4-fluoro-2-hydroxyphenyl)-2-pyridyl)fluoromethane (Example 10) and 20 ml of a 0.5N aluminum chloride solution in ethanol. Repeated recrystallization from DMSO (200 ml) gave 5.32 g (86.0%) of the pale yellow complex at a purity of 99.9% by $^1$H NMR.

$^1$H NMR (DMSO-d6): δ [ppm]=8.24 (dd, $^3J_{HH}$=8.0 Hz, $^3J_{HH}$=8.0 Hz, 3H, H-4-Py), 8.15 (d, $^3J_{HH}$=8.0 Hz, 3H, H-5-Py), 7.97 (dd, $^3J_{HH}$=8.0 Hz, $^4J_{FH}$=3.4 Hz, 3H, H-3-Py), 7.92 (dd, $^3J_{HH}$=9.0 Hz, $^4J_{FH}$=7.0 Hz, 3H, H-6), 6.53 (ddd, $^3J_{HH}$=8.7 Hz, $^3J_{FH}$=8.7 Hz, $^4J_{HH}$=2.7 Hz, 3H, H-5), 5.92 (dd, $^3J_{FH}$=11.4 Hz, $^4J_{HH}$=2.7 Hz, 3H, H-3).

$^{19}$F{$^1$H} NMR (DMSO-d6) δ [ppm]=−178.4 (s, 1F), −109.5 (s, 3F).

$T_g$: 197° C.

Comparative Experiments on Hydrolysis Stability

Example 16

In a comparative experiment, the hydrolysis stability of the polypodal aluminum complex mono[tris(6-(5-fluoro-2-oxyphenyl)-2-pyridyl)fluoromethanato]-aluminum(III) (Al—PPL-2), according to Example 13, was compared with that of the structurally analogous but not polypodal variant tris[5-fluoro-2-oxyphenyl)-2-pyridylato]aluminum(III), which is described in the application JP 09176629 A2 as an OLED material. To this end, a 10 mmolar solution of both complexes in dry DMSO-d6 was prepared under an inert gas atmosphere. This solution was characterized with the aid of $^1$H NMR and of $^{19}$F NMR spectroscopy. Subsequently, these solutions were admixed at room temperature with the 1000 molar amount of water and, after standing for 10 min, characterized again with the aid of $^1$H NMR and of $^{19}$F NMR spectroscopy. In the case of the polypodal aluminum complex mono[tris(6-(5-fluoro-2-oxyphenyl)-2-pyridyl)fluoromethanato]aluminum(III) (Al—PPL-2) according to Example 13, no change whatsoever in the NMR could be detected. In contrast, in the case of the non-polypodal tris(5-fluoro-2-oxyphenyl)-2-pyridylato)aluminum(III), full decomposition of the complex was observed, recognizable by appearance of the proton and fluorine signals of the noncoordinated ligands. Even after heating the above-described hydrolysis mixture to 180° C. for five hours, no sign of decomposition of the polypodal aluminum complex Al—PPL-2 according to Example 13 could be detected. This comparative experiment demonstrates clearly the excellent hydrolysis stability of the inventive polypodal complexes.

Production and Characterization of Organic Electroluminescent Devices which Comprise Inventive Compounds The OLEDs are produced by a general process which was optimized in the individual case to the particular circumstances (for example layer thickness variation to optimize the efficiency and the color). Inventive electroluminescent devices can be prepared as described, for example, in DE 10330761.3 or else DE 10261545.4.

Example 17

Device Structure

The examples which follow show the results of various OLEDs, both with phosphorescence emitters and fluorescence emitters, in which inventive compounds were used in the first case as hole blocking materials, and BCP and BAlq as comparative materials (see Table 1). In the second case, an inventive compound was used as the electron transport material and AlQ$_3$ as the corresponding comparative material (see Table 2). The basic structure, the materials and layer thicknesses used (apart from the HBLs) were identical for better comparability.

According to the abovementioned general process, phosphorescent OLEDs with the following structure were obtained:

| | |
|---|---|
| PEDOT (HIL) | 60 nm (spin coated from water; purchased as Baytron P from H. C. Starck; poly(3,4-ethylenedioxy-2,5-thiophene)) |
| NaphDATA (HTL) | 20 nm (applied by vapor deposition; purchased from SynTec; 4,4',4''-tris(N-1-naphthyl-N-phenylamino)triphenylamine) |
| S-TAD (HTL) | 20 nm (applied by vapor deposition; prepared according to WO 99/12888; 2,2',7,7'-tetrakis(diphenylamino)spirobifluorene) |
| (EML) | materials and layer thicknesses: see Table 1 or 2 |
| (HBL) | if present, materials and layer thicknesses: see Table 1 |
| (ETL) | materials and layer thicknesses: see Table 1 or 2 |
| Ba—Al (cathode) | 3 nm of Ba, 150 nm of Al thereon. |

These OLEDs which were yet to be optimized were characterized in a standard manner; for this purpose, the electroluminescence spectra, the efficiency (measured in cd/A), the power efficiency (measured in lm/W) were determined as a function of the brightness and the lifetime. The lifetime is defined as the time after which the starting brightness of the OLED has fallen by half at a constant current density of 10 mA/cm$^2$.

Table 1 compiles the results of the inventive OLEDs with use of the phosphorescence emitter Ir(PPY)$_3$ doped to an extent of 10% in CBP (4,4'-bis(carbazol-9-yl)biphenyl) and use of the complex Al—PPL2 according to Example 13 as a hole blocking material, and a comparative example (with BAlq). Table 1 shows merely the hole blocking layer and the electron transport layer (composition and layer thickness). The electron transport material used was AlQ$_3$ (tris(8-hydroxyquinolinato)aluminum(III)), purchased from SynTec. The other layers correspond to the abovementioned structure.

Table 2 compiles the results of the inventive OLEDs with use of a fluorescence emitter and use of the complex Al—PPL2 according to Example 13 as the electron transport material, and some comparative examples (with the electron transport material AlQ$_3$). Table 2 shows merely the emitter layer and the electron transport layer (composition and layer thickness). The other layers correspond to the abovementioned structure.

The abbreviations used above and in Tables 1 and 2 correspond to the following compounds:

TABLE 1

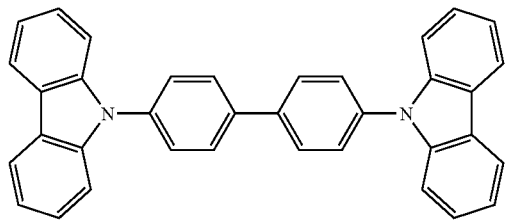

CBP

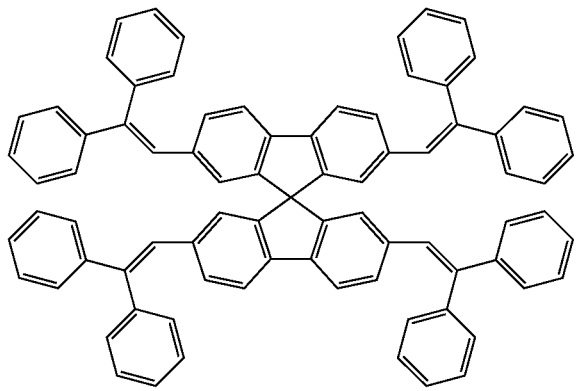

S-DPVBi

TABLE 1-continued

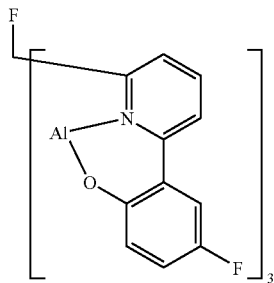

Al-PPL02, according to Ex. 13

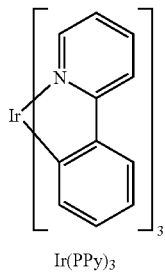

Ir(PPy)₃

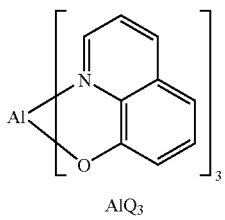

AlQ₃

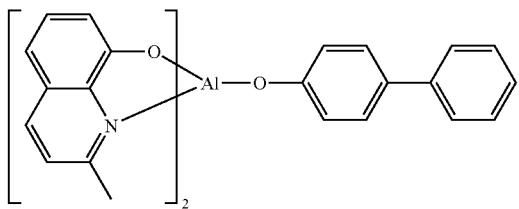

BAlq

| Example | HBL | ETL | Max. efficiency (cd/A) | Voltage (V) at 100 cd/m$^2$ | Power efficiency (lm/W) at max. efficiency | CIE (x, y) | Lifetime (h) at 10 mA/cm$_2$ |
|---|---|---|---|---|---|---|---|
| Example T1 | Al-PPL2 (10 nm) | AlQ₃ (20 nm) | 30.0 | 5.1 | 16.5 | 0.32/0.62 | 600 |
| Example T2 (comparison) | BAlq (10 nm) | AlQ₃ (20 nm) | 18.3 | 5.1 | 8.5 | 0.32/0.62 | 250 |
| Example T3 | Al-PPL2 (20 nm) | — | 22.9 | 3.2 | 23.2 | 0.32/0.62 | 290 |
| Example T4 (comparison) | BAlq (20 nm) | — | 16.5 | 5.3 | 8.8 | 0.32/0.62 | 180 |

TABLE 2

| Example | EML | ETL | Max. efficiency (cd/A) | Voltage (V) at 100 cd/m$^2$ | Power efficiency (lm/W) at max. efficiency | CIE (x, y) | Lifetime (h) at 10 mA/cm$_2$ |
|---|---|---|---|---|---|---|---|
| Example S1 | S-DPVBi (30 nm) | Al-PPL2 (10 nm) | 4.7 | 3.6 | 3.8 | 0.16/0.20 | 800 |
| Example S2 (comparison) | S-DPVBi (30 nm) | Al-Q₃ (10 nm) | 3.9 | 4.9 | 2.4 | 0.16/0.20 | 640 |

Table 1 shows that the use of Al—PPL2 in phosphorescent OLEDs as the hole blocking material distinctly increases the efficiency, in particular the power efficiency, of the OLEDs in comparison to BAlq, and typically a doubling of the power efficiency was observed. At the same time, the lifetime was also distinctly improved. The examples show that even the electron transport layer can be left out, which constitutes a distinct simplification of the device structure.

In the case of the use of Al—PPL2 as the electron transport material in fluorescent OLEDs, the efficiency, power efficiency and lifetime are likewise distinctly improved, as can be taken from Table 2.

In summary, it can be stated that phosphorescent and fluorescent OLEDs which comprise inventive compounds such as Al—PPL2 as hole blocking materials or electron transport materials have high efficiencies with simultaneously long lifetimes and low operating voltages, as can be taken readily from the examples listed in Tables 1 and 2.

What is claimed is:

1. A compound of the structure 1,

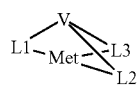

structure 1 containing at least one metal Met, wherein Met is a transition metal, Group III metal or f-block metal, coordinated to a polypodal ligand Lig of the structure 2,

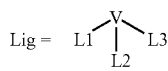

structure 2 where V is a bridging unit, characterized in that the three part-ligands L1, L2 and L3 which may be the same or different at each instance are covalently bonded to one another, and where V is CR, COH, $COR^1$, CF, CCl, CBr, C—I, $CN(R^1)_2$, $RC(CR_2)_3$, $RC(SiR_2)_3$;

R is the same or different at each instance and is H, F, Cl, Br, I, $NO_2$, CN, a straight-chain or branched or cyclic alkyl or alkoxy group having from 1 to 20 carbon atoms, in which one or more nonadjacent $CH_2$ groups may be replaced by $-R^1C=CR^1-$, $-C\equiv C-$, $Si(R^1)_2$, $Ge(R^1)_2$, $Sn(R^1)_2$, $C=O$, $C=S$, $C=Se$, $C=NR^1$, $-O-$, $-S-$, $-NR^1-$ or $-CONR^1-$, and in which one or more hydrogen atoms may be replaced by F, or an aryl or heteroaryl group which has from 1 to 14 carbon atoms and may be substituted by one or more nonaromatic R radicals, where a plurality of substituents R, both on the same ring and on the two different rings, together may in turn form a further mono- or polycyclic, aliphatic or aromatic ring system;

$R^1$ is the same or different at each instance and is an aliphatic or aromatic hydrocarbon radical having from 1 to 20 carbon atoms;

and where the three part-ligands L1, L2 and L3 satisfy the structure 3

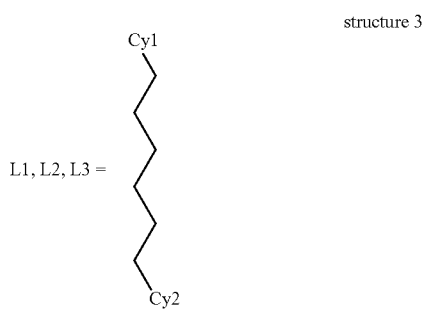

structure 3 where Cy1 is a substituted or unsubstituted 2-pyridyl connected to V and Cy2 are the same or different at each instance and correspond to substituted or unsubstituted aromatic homocycles of carbon or substituted or unsubstituted aromatic heterocycles, which are each bonded ionically, covalently or coordinatively to the metal via a ring atom or via an atom bonded exocyclically to the homo- or heterocycle, the zig-zag line is a direct bond linkage between Cy1 to Cy2, and that the compounds of the structure 1 are uncharged.

2. The compound as claimed in claim 1, wherein L1=L2=L3.

3. The compound as claimed in claim 1, wherein the polypodal ligand Lig of the structure 4 generates facial coordination geometry on the metal Met

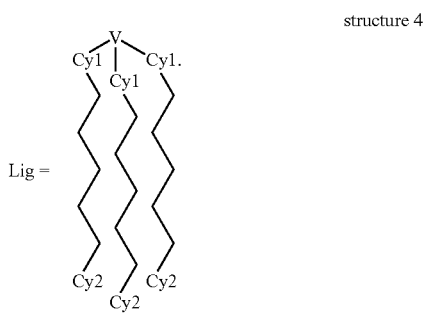

structure 4

4. A metal complex which comprises the compound as claimed in claim 1, selected from the compounds $(1)^1$ and $(2)^1$,

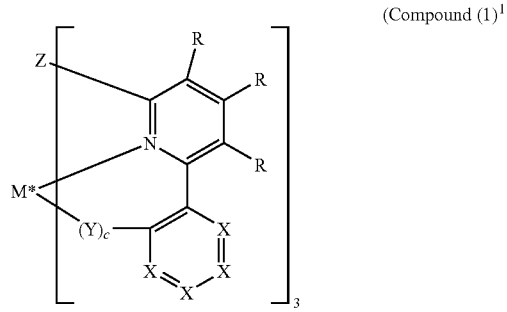

(Compound $(1)^1$)

-continued

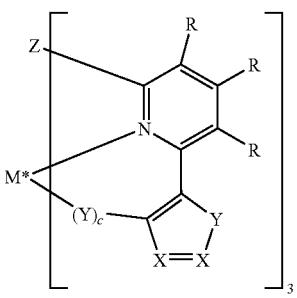

(Compound (2))₁ where the symbols and indices are each defined as follows:

M is Al, Ga, In, Tt, P, As, Sb, Bi, Sc, Y, La, V, Nb, Ta, Cr, Mo, W, Fe, Ru, Os, Co, Rh, Ir, Cu, Au, Pr, Nd, Sm, Eu, Gd, Tb, Dy, Ho, Er, Tm, Yb or Lu;

X is the same or different at each instance and is CR, N or P;

Y is the same or different at each instance and is $NR^1$, O, S, Se, Te, SO, SeO, TeO, $SO_2$, $SeO_2$ or $TeO_2$;

Z is the same as defined for V

R is the same or different at each instance and is H, F, Cl, Br, I, $NO_2$, CN, a straight-chain or branched or cyclic alkyl or alkoxy group having from 1 to 20 carbon atoms, in which one or more nonadjacent $CH_2$ groups may be replaced by —$R^1C$=$CR^1$—, —C≡C—, $Si(R^1)_2$, $Ge(R^1)_2$, $Sn(R^1)_2$, C=O, C=S, C=Se, C=$NR^1$, —O—, —S—, —$NR^1$— or —$CONR^1$—, and in which one or more hydrogen atoms may be replaced by F, or an aryl or heteroaryl group which has from 1 to 14 carbon atoms and may be substituted by one or more nonaromatic R radicals, where a plurality of substituents R, both on the same ring and on the two different rings, together may in turn form a further mono- or polycyclic, aliphatic or aromatic ring system; and $R^1$ is the same or different at each instance and is an aliphatic or aromatic hydrocarbon radical having from 1 to 20 carbon atoms and c is the same or different at each instance and is 0 or 1.

5. The metal complex as claimed in claim 4, wherein the symbol M=Al, Ga, In, Sc, Y, La, Ru, Os, Rh, Ir or Au.

6. The metal complex as claimed in claim 4, wherein the symbol X=CR.

7. The metal complex as claimed in claim 4, wherein the symbol Y=O or S.

8. The metal complex as claimed in claim 4, wherein the symbol R=H, F, Cl, Br, I, CN, a straight-chain or branched or cyclic alkyl or alkoxy group having from 1 to 6 carbon atoms or an aryl or heteroaryl group which has from 3 to 8 carbon atoms and may be substituted by one or more nonaromatic R radicals, in which a plurality of substituents R, either on the same ring or on the two different rings, together may in turn form a further mono- or polycyclic, aliphatic or aromatic ring system.

9. The compound as claimed in claim 1, wherein the compound has a purity (determined by means of $^1$H NMR and/or HPLC) is more than 99%.

10. Conjugated, semiconjugated or nonconjugated polymers or dendrimers containing one or more compounds of the structure (1) as claimed in claim 1.

11. Conjugated, semiconjugated or nonconjugated polymers or dendrimers as claimed in claim 10, in which one or more of the R radicals is a bond to the polymer or dendrimer and R is the same or different at each instance and is H, F, Cl, Br, I, $NO_2$, CN, a straight-chain or branched or cyclic alkyl or alkoxy group having from 1 to 20 carbon atoms, in which one or more nonadjacent $CH_2$ groups may be replaced by —$R^1C$=$CR^1$—, —C≡C—, $Si(R^1)_2$, $Ge(R^1)_2$, $Sn(R^1)_2$, C=O, C=S, C=Se, C=$NR^1$, —O—, —S—, —$NR^1$— or —$CONR^1$—, and in which one or more hydrogen atoms may be replaced by F, or an aryl or heteroaryl group which has from 1 to 14 carbon atoms and may be substituted by one or more nonaromatic R radicals, where a plurality of substituents R, both on the same ring and on the two different rings, together may in turn form a further mono- or polycyclic, aliphatic or aromatic ring system; and $R^1$ is the same or different at each instance and is an aliphatic or aromatic hydrocarbon radical having from 1 to 20 carbon atoms.

12. Polymers as claimed in claim 10, characterized in that the polymer is selected from the group of polyfluorenes, poly-spiro-bifluorenes, poly-para-phenylenes, polycarbazoles, polyvinylcarbazoles, polythiophenes, or else from copolymers which have a plurality of the units specified here.

13. Polymers as claimed in claim 10, characterized in that the polymer is soluble in organic solvents.

14. An electronic component comprising at least one compound as claimed in claim 1.

15. The electronic component as claimed in claim 14, characterized in that it is an organic light-emitting diode (OLED), organic integrated circuit (O-IC), organic field-effect transistor (OFET), organic thin-film transistor (OTFT), organic solar cell (O-SC) or organic laser diode (O-laser).

16. An electronic component comprising a polymer or dendrimer as claimed in claim 10.

* * * * *